US011123462B2

(12) United States Patent
Ochiai

(10) Patent No.: US 11,123,462 B2
(45) Date of Patent: Sep. 21, 2021

(54) MANUAL BREAST PUMP

(71) Applicant: PIGEON CORPORATION, Tokyo (JP)

(72) Inventor: Yukifumi Ochiai, Tokyo (JP)

(73) Assignee: PIGEON CORPORATION, Tokyo (JP)

( * ) Notice: Subject to any disclaimer, the term of this patent is extended or adjusted under 35 U.S.C. 154(b) by 86 days.

(21) Appl. No.: 16/300,320

(22) PCT Filed: May 11, 2017

(86) PCT No.: PCT/JP2017/017947
§ 371 (c)(1),
(2) Date: Nov. 9, 2018

(87) PCT Pub. No.: WO2017/195876
PCT Pub. Date: Nov. 16, 2017

(65) Prior Publication Data
US 2019/0143014 A1  May 16, 2019

(30) Foreign Application Priority Data

May 11, 2016  (JP) .............................. JP2016-095498

(51) Int. Cl.
*A61M 1/06* (2006.01)
*A61M 1/00* (2006.01)

(52) U.S. Cl.
CPC .............. *A61M 1/064* (2014.02); *A61M 1/06* (2013.01); *A61M 1/82* (2021.05);
(Continued)

(58) Field of Classification Search
CPC ........ A61M 1/06; A61M 1/062; A61M 1/064; A61M 1/066; A61M 1/0072; A61M 1/068;
(Continued)

(56) References Cited

U.S. PATENT DOCUMENTS 8,187,219 B1   5/2012  Chiang
2003/0191432 A1*  10/2003  Silver .................. A61M 1/062
604/74

(Continued)

FOREIGN PATENT DOCUMENTS

CN    103656769 A   3/2014
EP     2708248 A1   3/2014
(Continued)

OTHER PUBLICATIONS

The extended European search report of the corresponding EP application No. 17796234.7 dated Apr. 16, 2019.

*Primary Examiner* — Amber R Stiles
*Assistant Examiner* — Alexandra Lalonde
(74) *Attorney, Agent, or Firm* — Muncy, Geissler, Olds & Lowe, P.C.

(57) ABSTRACT

A manual breast pump includes: a body having a communicating part that communicates with space surrounded by a hood placed on a breast; a diaphragm that deforms to generate a negative pressure in the communicating part; and a handle for operation that approaches and separates from the body, wherein a colliding part, against which at least the handle and the body collide before directly contacting each other, is provided in at least a region of any of the handle, the body, and the diaphragm, the colliding part is integrally made of a same material as a material of a region in which the colliding part is arranged, and has a damper structure that absorbs an impulsive force or reduces propagation of the impulsive force and/or a cover structure in which the colliding part is covered via a gap so as not to be exposed to an outside.

18 Claims, 12 Drawing Sheets

(52) U.S. Cl.
CPC ............... *A61M 2205/071* (2013.01); *A61M 2205/3337* (2013.01); *A61M 2205/42* (2013.01)

(58) Field of Classification Search
CPC ........ A61M 2205/42; A61M 2205/071; A61M 1/82; A61M 1/069; A61M 1/0693; A61M 1/06935; A61M 1/0697; A61M 1/067; A61M 2205/3337
See application file for complete search history.

(56) References Cited

U.S. PATENT DOCUMENTS

| | | | |
|---|---|---|---|
| 2005/0154348 A1 | 7/2005 | Lantz et al. | |
| 2008/0208115 A1* | 8/2008 | Kliegman | A61M 1/0068 604/74 |
| 2013/0072866 A1 | 3/2013 | Hegen | |
| 2014/0088495 A1* | 3/2014 | Behrens | A61M 1/066 604/74 |

FOREIGN PATENT DOCUMENTS

| | | |
|---|---|---|
| EP | 2875835 B1 | 12/2016 |
| JP | 2005-521522 A | 7/2005 |
| JP | 2013-528096 A | 7/2013 |
| WO | 03/013628 A1 | 2/2003 |

\* cited by examiner

FIG. 17

| | BODY | | HANDLE | | DIAPHRAGM | |
|---|---|---|---|---|---|---|
| 1 | CONVENTIONAL TYPE MOLDED ARTICLE | | CONVENTIONAL TYPE MOLDED ARTICLE | | CONVENTIONAL TYPE MOLDED ARTICLE | |
| 2 | CONVENTIONAL TYPE 3D PRINTER | | CONVENTIONAL TYPE 3D PRINTER | | CONVENTIONAL TYPE MOLDED ARTICLE | |
| 3 | COLLIDING COVER 3D PRINTER | | CONVENTIONAL TYPE 3D PRINTER | | CONVENTIONAL TYPE MOLDED ARTICLE | |
| 4 | COLLIDING COVER +SPRING SHAPE 3D PRINTER | | CONVENTIONAL TYPE 3D PRINTER | | CONVENTIONAL TYPE MOLDED ARTICLE | |
| 5 | CONVENTIONAL TYPE 3D PRINTER | | COLLIDING PART HAVING SPRING SHAPE 3D PRINTER | | CONVENTIONAL TYPE MOLDED ARTICLE | |
| 6 | CONVENTIONAL TYPE 3D PRINTER | | CONVENTIONAL TYPE 3D PRINTER | | PROTRUDING COLLIDING PART CAST ARTICLE | |
| 7 | CONVENTIONAL TYPE MOLDED ARTICLE | | CONVENTIONAL TYPE MOLDED ARTICLE | | PROTRUDING COLLIDING PART CAST ARTICLE | |

FIG. 18

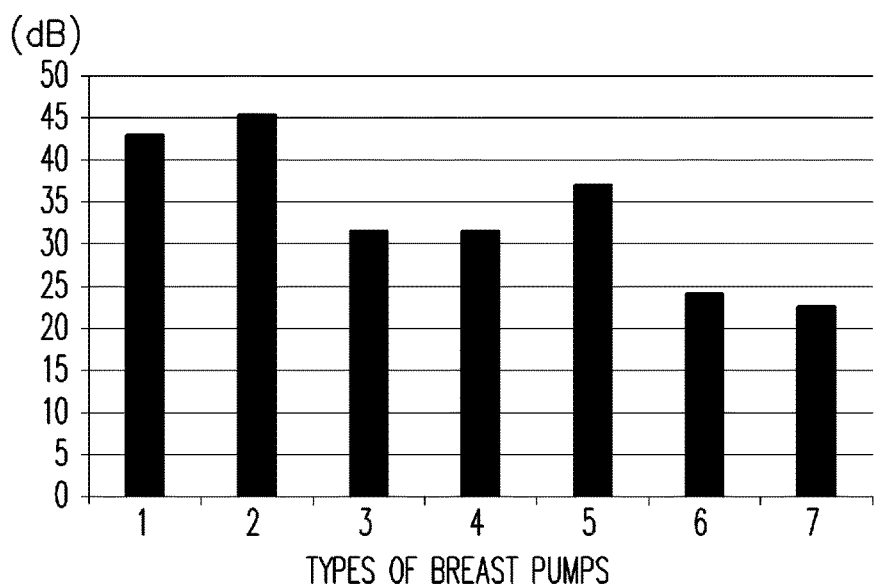

MANUAL BREAST PUMP

TECHNICAL FIELD

The present invention relates to a manual breast pump for manually expressing breast milk.

BACKGROUND ART

Conventionally, manual breast pumps with which users manually express breast milk have been known. PTL 1 shows an example of such a manual breast pump. As shown in FIG. 1 of PTL 1, the manual breast pump has a hood member 12 that covers the breast of a user, a housing 24 connected to the hood member 12, and a pump 14 for applying a negative pressure to the housing 24. Breast milk is sucked from a nipple put to the hood member 12 via the housing 24, using a negative-pressure state generated by the pump 14.

The pump 14 is constituted by a diaphragm, and the diaphragm deforms with the operation of a connected lever 34 to thereby generate the above negative-pressure state. The lever 34 is manually rotated and operated so as to approach and separate from the housing 24.

Here, the user grasps the lever 34 and the housing 24 with one hand at the same time to rotate and operate the lever 34. Therefore, the lever 34 and the housing 24 have dimensions at which the user is allowed to grasp the lever 34 and the housing 24 with one hand. Under such a condition, the user is required to greatly rotate the lever 34 as much as possible to generate a great negative pressure and substantially express breast milk. As a result, the lever 34 and the housing 24 made of rigid plastic collide against each other, and a sound generated by the collision between the rigid plastic makes the user uncomfortable as a noise.

In PTL 1, in consideration of such circumstances, a compressible material 40 made of elastomer, natural rubber, or the like is provided at the position of the housing 24 that collides against the lever 34 to reduce the collision sound with the compressible material 40.

CITATION LIST

Patent Literature

[PTL 1] Japanese Translation of PCT Application Publication No. 2005-521522

SUMMARY OF INVENTION

Technical Problem

However, when the breast pump is so structured that the compressible material 40 is provided in the housing 24 made of the rigid plastic, the compressible material 40 having a greater area is required to be bonded to or wound on the housing 24 to prevent the compressible material 40 from peeling off or coming off the housing 24. Particularly, since the lever 34 repeatedly collides against the compressible material 40 many times, the bonding or winding amount of the compressible material 40 to the housing 24 should be increased considerably. For this reason, the weight of the manual breast pump is increased, which causes the fatigue of the user on the contrary.

In addition, when the compressible material 40 for collision-sound proofing is used besides the rigid plastic, a manufacturing cost is also increased.

It is an object of the present invention to provide an inexpensive manual breast pump that lessens fatigue while reducing the collision sound between a handle and a body.

Solution to Problem

According to the present invention, the above problem is solved by a manual breast pump including: a body having a communicating part that communicates with space surrounded by a hood placed on a breast; a diaphragm that deforms to generate a negative pressure in the communicating part; and a handle for operation that approaches and separates from the body to deform the diaphragm, wherein a colliding part, against which at least the handle and the body collide before directly contacting each other when the handle approaches the body, is provided in at least a region of any of the handle, the body, and the diaphragm, the colliding part is integrally made of a same material as a material of the region in which the colliding part is arranged, and the colliding part or a collided part has a damper structure that absorbs an impulsive force generated when making the collision or reduces propagation of the impulsive force.

The above configuration includes the body having the communicating part that communicates with the space surrounded by the hood, the diaphragm that deforms to generate a negative pressure in the communicating part, and the handle for operation that approaches and separates from the body to deform the diaphragm. Therefore, when the handle is operated to deform the diaphragm, the handle is liable to collide against the body.

However, when the handle approaches the body, the colliding part, against which at least the handle and the body collide before directly contacting each other, is provided in at least a region of any of the handle, the body, and the diaphragm. Accordingly, the colliding part is interposed between the handle and the body and/or between the handle and the diaphragm and makes a collision before the handle and the body collide against each other. Thus, since the collision between the handle and the body is prevented, the occurrence of an uncomfortable colliding sound can be prevented. Alternatively, even if the handle and the body collide against each other by the operation of the handle, the colliding part makes a collision beforehand and thus an impact caused by the collision between the handle and the body is alleviated. As a result, the collision sound can be reduced.

Here, the colliding part is integrally made of the same material as that of the region of any of the handle, the body, and the diaphragm in which the colliding part is arranged. Therefore, even if the colliding part repeatedly makes a collision, an accident in which the colliding part comes off any of the handle, the body, and the diaphragm in which the colliding part is arranged can be prevented as much as possible. Further, the colliding part is not required to be connected in a great amount correspondingly. Accordingly, fatigue during use can be lessened with a reduction in the weight of the manual breast pump, and the manual breast pump can be manufactured at a low cost.

Further, the colliding part or a collided part against which the colliding part collides has a damper structure. When the collision part makes a collision, the damper structure can weaken the collision force itself to reduce the occurrence of the collision sound or reduce a propagation sound inside the collision part (solid object). Accordingly, even if the colliding part makes a collision before the handle and the body collide against each other, quietness can be improved.

In addition, the body has preferably a base part that has higher rigidity than the diaphragm and serves as a base to which the diaphragm is connected, the colliding part is preferably provided in the diaphragm and/or a region of the handle that approaches the diaphragm during an operation of the handle, and the impulsive force generated when the colliding part makes a collision preferably acts on a connecting region of the diaphragm that is connected to the base part.

Thus, the impulsive force generated when the colliding part makes a collision is applied to the connecting region connected to the base part, but the connecting region itself is a region not substantially related to a negative-pressure generating function representing the original function of the diaphragm. Accordingly, even if the diaphragm is used as the damper structure, an adverse effect on the negative-pressure generating function of the breast pump can be prevented, and the expressing of milk can be appropriately realized. Note that the preferred invention does not exclude a configuration the impulsive force during the collision of the colliding part acts not only on the connecting region of the diaphragm but also on a portion other than the connecting region of the diaphragm. When the impulsive force acts also on the portion other than the connecting region, the impulsive force generated when the colliding part makes the collision preferably acts on the connecting region of the diaphragm with priority.

In addition, the colliding part preferably protrudes from the connecting region so as to be capable of colliding against the handle.

Thus, as described above, since the colliding part is integrally made of the same material as that of a region in which the colliding part is arranged, the colliding part formed to protrude from the connecting region of the diaphragm connected to the base part also exhibits the same deformation force as that of the diaphragm. Thus, the colliding part can absorb the impulsive force and reduce the collision sound. Particularly, since the diaphragm is made of silicon rubber or the like and characterized in its deformation easiness through a manual operation, the colliding part easily deforms similarly. Accordingly, the colliding part also has considerably high impulse absorption and thus can realize high quietness.

In addition, since the colliding part protrudes from the connecting region connected to the rigid base part by fitting or the like, an adverse effect on the negative-pressure generation portion of the diaphragm by the impulsive force can also be prevented. As a result, the expressing of milk can be appropriately realized.

Moreover, the attachment and detachment of the base part and the diaphragm is facilitated with the protruding colliding part as a knob.

In addition, the colliding part preferably has a notched part or a concave part at a root or a halfway point thereof in a direction of the protrusion.

Thus, stress generated when the colliding part makes a collision and deforms is focused on the notched part or the concave part. Therefore, the deformation of the diaphragm at the negative-pressure generation portion due to a collision can be more effectively prevented, and an adverse effect on the original pumping function of the diaphragm can be effectively prevented.

In addition, the colliding part preferably protrudes from a circumference of the connecting region surrounding the base part.

Thus, the colliding part is arranged so as to surround the circumference of the base part. When rotated around the base part, the colliding part can collide against the handle at any position.

Further, when the colliding part is rotated as described above, the portion of the diaphragm integrally formed with the colliding part and covering the communicating part also rotates. Accordingly, the unevenness of degradation partially occurring in the diaphragm is prevented by the rotation of the diaphragm at any timing, and thus the service life of the diaphragm can be extended. Particularly, when the handle pivotally supported on its one side is rotated to deform the diaphragm, there is a likelihood that the diaphragm unevenly deforms and partially sags. However, the partial sagging of the diaphragm can be prevented by the rotation of the diaphragm.

In addition, the colliding part is preferably a protruding part that protrudes from the handle, at least a part of the collided part is preferably the connecting region of the diaphragm, and the colliding part preferably collides against a surface in a thickness direction of the collided region.

Thus, since the colliding part is the protruding part that protrudes from the handle, the colliding part can be manufactured at a low cost compared with the above colliding part formed to protrude from the diaphragm made of silicon rubber or the like.

In this regard, the above colliding part that protrudes from the diaphragm produces an excellent effect for quietness, but there is a likelihood that the colliding part is liable to be folded after colliding against the handle and a sense of discomfort is given to a user due to its deformation easiness. However, the preferred invention includes a configuration in which the colliding part is formed to protrude from the handle more rigid than the diaphragm and collides against the surface in the thickness direction of the collided region (that is, the connecting region of the diaphragm that is connected to the base part). Thus, both the colliding part and the collided part are made hardly foldable. Accordingly, the operation of the handle is smoothened, whereby a sense of discomfort given to the user can be prevented.

Note that in the preferred invention, it is sufficient that at least a part of the collided part serves as the connecting region of the diaphragm that is connected to the base part (or the whole collided region may be the connecting region). When at least a part of the collided part is the connecting region, it is not possible to make the handle approach the side of the body further than the rigid base part. Therefore, the collided part is hardly foldable, and an adverse effect on the negative-pressure generating function of the diaphragm can be effectively prevented.

In addition, a lever part of the handle preferably has an elastic force in a direction in which the handle approaches the body, and exhibits the elastic force to be capable of contacting the body after the colliding part collides against the collided part.

Accordingly, when the user further strongly grasps the lever part after the colliding part and the collided part collide against each other, the lever part and the body easily contact each other to allow the user to have a sense of fulfillment in that the he/she has grasped the lever part to the end. On this occasion, even if the lever part and the body abut against each other, an impact force is first weakened by the damper structure as described above. In addition, an accident in which the lever part makes a strong collision can be prevented due to its elastic force. Accordingly, the manual breast pump exhibits excellent quietness.

According to the present invention, the above problem is solved by a manual breast pump including: a body having a communicating part that communicates with space surrounded by a hood placed on a breast; a diaphragm that deforms to generate a negative pressure in the communicating part; and a handle for operation that approaches and separates from the body to deform the diaphragm, wherein a colliding part, against which at least the handle and the body collide before directly contacting each other when the handle approaches the body, is provided in at least a region of any of the handle, the body, and the diaphragm, the colliding part is integrally made of a same material as a material of the region in which the colliding part is arranged, and the colliding part is structured to be covered via a gap so as not to be exposed to an outside when making the collision.

According to the above configuration, when the handle approaches the body, the colliding part, against which at least the handle and the body collide before directly contacting each other, is provided in the region of any of the handle, the body, and the diaphragm. Therefore, similarly to the invention described above, the colliding part makes a collision before the handle and the body contact each other. Thus, the collision between the handle and the body is prevented, or an impact caused by the collision between the handle and the body is alleviated. As a result, the collision sound can be reduced.

In addition, the colliding part is integrally made of the same material as that of the region of any of the handle, the body, and the diaphragm in which the colliding part is arranged. Therefore, as described above, the colliding part is not required to be connected in a large amount to the handle, the body, and the body to be prevented from coming off. Accordingly, fatigue during use can be lessened with a reduction in the weight of the manual breast pump, and the manual breast pump can be manufactured at a low cost.

Further, the colliding part has a cover structure in which the colliding part is covered via a gap so as not to be exposed to an outside during a collision. Accordingly, a collision sound generated during the collision is confined inside the cover structure and can hardly propagate through a user. Note that if the gap is not present between the colliding part and a member covering the colliding part, the collision sound immediately leaks to the outside. However, in the present invention, the exposure of the collision sound to the outside can be effectively prevented by the gap.

In addition, the handle preferably has a cavity part opened toward a side of the body, and the colliding part is preferably arranged inside the cavity part at least during the collision.

Accordingly, when the handle collides against the body, the colliding part that has made a collision is present inside the cavity part. Thus, the collision sound is effectively confined inside the cavity part and can be prevented from reaching an outside user. Note that the colliding part may be provided on the side of the body or on the side of the handle so long as the colliding part is allowed to be arranged inside the cavity part during the collision.

In addition, when the colliding part is arranged inside the cavity part of the handle during a collision as described above, the handle is preferably rotatable about a support shaft part of the body and the colliding part is preferably arranged around the support shaft part of the body.

Thus, the end of the handle on its side opposite to the shaft support is not required to be increased to hide the cavity part for hiding the colliding part. Accordingly, there is no likelihood that the rotated handle immediately contacts the body when the end is set to have a typical size, and the handle is set to have the same movement amount as a typical movement amount to make it possible to reliably deform the diaphragm. In addition, the weight of the end of the handle does not become heavy, and thus the user does not feel an unnecessary weight in the operation of the handle.

In addition, the colliding part preferably has a through-hole, and a colliding side relative to the through-hole is preferably deformable toward a side of the through-hole during the collision.

Thus, since the colliding part has the through-hole, stress caused by an impact is easily focused on the periphery of the through-hole and can be prevented from propagating through a region other than the colliding part. Accordingly, even if the colliding part is integrally formed with the body or the handle, a collision sound can be reduced.

In addition, the colliding side relative to the through-hole is deformable toward the side of the through-hole during a collision. Therefore, even if the colliding part is made of a material having relatively high rigidity, an impulsive force can be effectively absorbed with an increase in the deformation amount of the colliding part.

Advantageous Effects of Invention

As described above, the present invention can provide an inexpensive manual breast pump that lessens fatigue while reducing the collision sound between a handle and a body.

BRIEF DESCRIPTION OF DRAWINGS

FIG. 17 is an outline view of the types of manual breast pumps used when noise measurement experiments were conducted.

FIG. 18 is a comparative diagram in which the noise levels of the respective manual breast pumps in FIG. 17 are compared with each other.

DESCRIPTION OF EMBODIMENTS

Hereinafter, preferred embodiments of the present invention will be described in detail with reference to the accompanying drawings.

Note that various technically preferable limitations are imposed on the following embodiments since the embodiments are suitable specific examples of the present invention, but the scope of the present invention is not limited to the modes unless otherwise specifically limited in the following descriptions. In addition, the same symbols attached in respective figures have the same configurations.

First Embodiment

A manual breast pump is used in a case in which it is difficult to directly feed breast milk to a baby, a case in which a nipple is damaged, a case in which mastitis is prevented, or the like, and is a tool with which a user can express milk through a manual operation. Since the user operates the manual breast pump for herself, the manual breast pump is preferably one that is lightweight, allows an operation with one hand, and can lessen fatigue.

Figure 1:
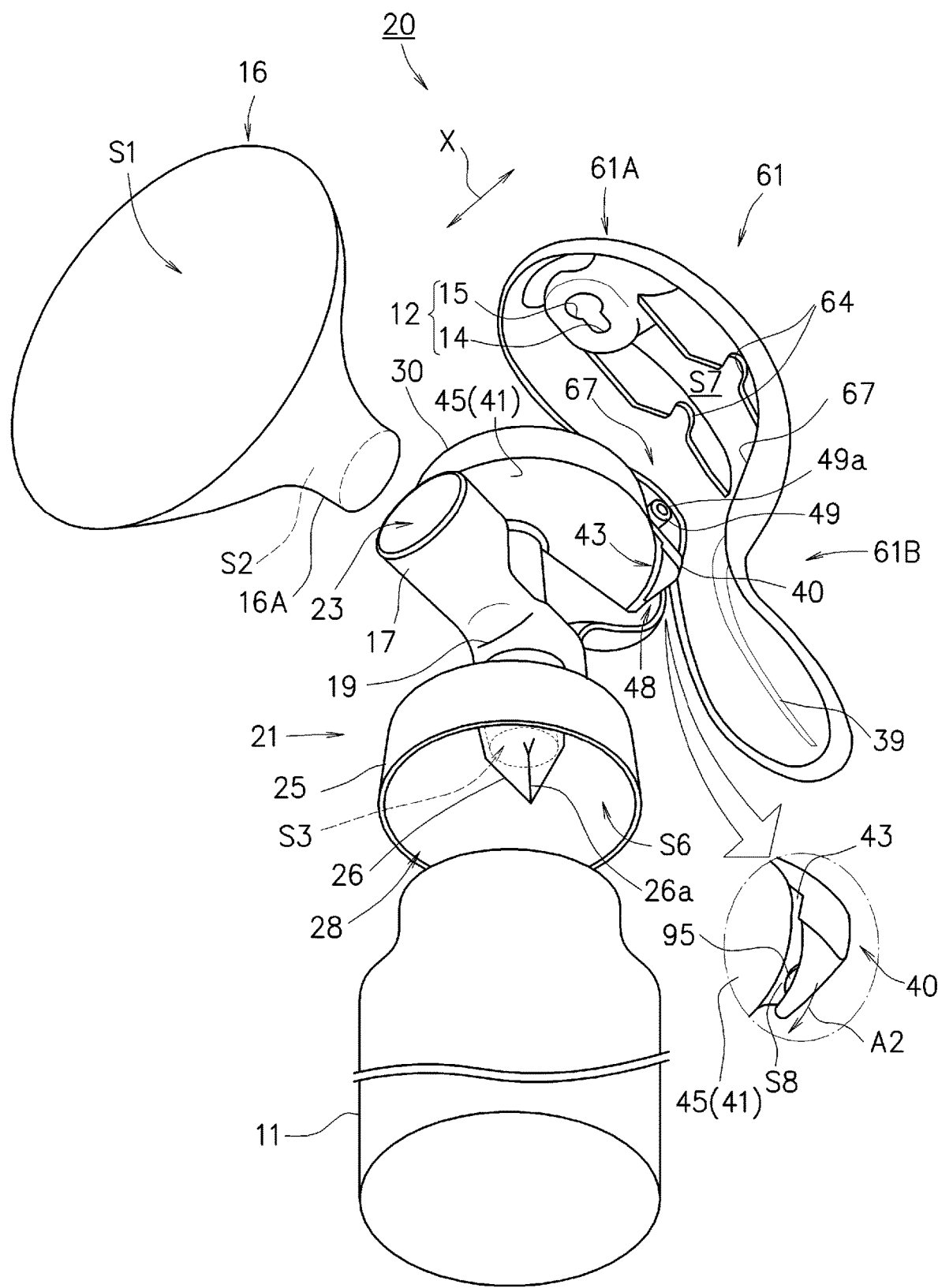
FIG. 1 is an exploded perspective view of a manual breast pump according to a first embodiment of the present invention.
Figure 2:
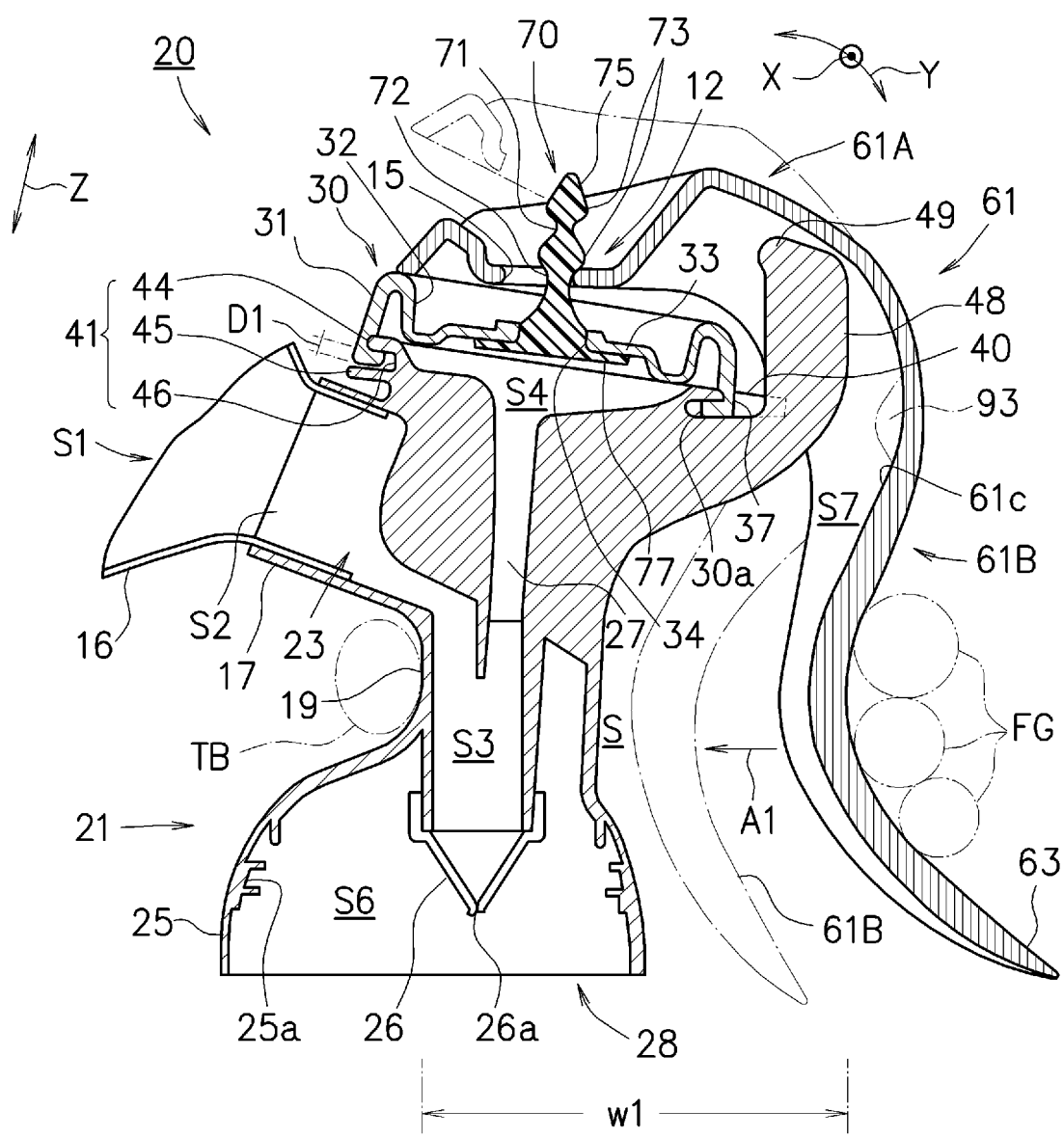
FIG. 2 is a substantially central longitudinal cross-sectional view of the manual breast pump in which parts in FIG. 1 are combined together.

FIGS. 1 and 2 show a first embodiment of such a manual breast pump (hereinafter abbreviated as a "breast pump"). FIG. 1 is an exploded perspective view of the breast pump, and FIG. 2 is a substantially central longitudinal cross-sectional view of the breast pump. Note that a view surrounded by dashed lines in FIG. 1 is an enlarged view in the vicinity of a colliding part 40. Further, a bottle 11 that will be described later is omitted in FIG. 2.

In the figures, the breast pump 20 includes: a "hood 16" placed on a breast; a "body 21" having a communicating part S4 that is space communicating with space S1 surrounded by the hood 16; a "diaphragm 30" that is a negative-pressure generating member for generating a negative pressure in the communicating part S4 of the body 21; a "handle 61" that is an operating part for deforming the diaphragm 30; and the "bottle 11" serving as an accommodation container for storing expressed breast milk.

The hood 16, the diaphragm 30, the handle 61, and the bottle 11 of the present embodiment are attachable/detachable to/from the body 21 as a preferable mode, but the present invention is not limited to this. The hood 16, the diaphragm 30, the handle 61, and the bottle 11 may be fixed to the body 21.

[Hood]

The hood 16 has a trumpet shape or a substantially dome shape corresponding to the shape of a breast, and has a reduced-diameter part 16A having the smallest diameter connected to the upper part of the body 21. A breast is placed in the space S1 surrounded by the hood 16 in use. When the breast is placed in the hood 16, the space S1 has accommodation space S2 for accommodating a nipple so as to be sealed and the pressure inside the accommodation space S2 is structured to be made negative to express milk.

[Body]

The body 21 is totally made of a synthetic resin material that is relatively light and rigid, and is made of, for example, polypropylene, polycarbonate, polycycloolefin, polyethersulfone, polyphenylsulfone, or the like.

An attachment part 17 to which the hood 16 of the body 21 is attached has a cylindrical shape and has an air passage 23 serving as a passage through which air and expressed breast milk pass. The air passage 23 is a first air passage 23 and spatially connected to the communicating part S4 via internal space S3 and a second air passage 27 formed at a substantially central part in the body 21 as shown in FIG. 2.

The communicating part S4 is a region in which a negative pressure is applied and has a base part 41 serving as a base to which the diaphragm 30 is attachably/detachably connected. The base part 41 of the present embodiment totally has a flange shape or a collar shape, and the diaphragm 30 that is expanded is hooked and connected to the base part 41. Specifically, as shown in FIG. 2, the base part 41 has outward double cylindrical flanges including a first flange 44 that protrudes outward and a second flange 45 that is placed under the first flange 44 and serves as positioning means having a diameter greater than that of the first flange 44. The base part 41 has an outwardly-opened outer groove 46 representing a cylindrical groove part that enters an inside thereof with the diameter between the first flange 44 and the second flange 45 reduced. Note that the shape of the base part 41 according to the present invention is not limited to a flange shape or a collar shape as in the present embodiment so long as the base part 41 is configured to be capable being connected to the diaphragm 30 so as to cover and seal the communicating part S4. For example, the shape of the base part 41 may be a cylindrical shape, a cup shape, or the like having a wall part with a substantial height to surround the periphery of the space of the communicating part S4 to which a negative pressure is applied.

When the diaphragm 30 is connected to the base part 41 so as to cover the communicating part S4 as described above and the pressure inside the communicating part S4 is made negative by the deformation of the diaphragm 30, the pressure inside space S1 surrounded by the hood 16 can be made negative via the second air passage 27, the internal space S3, and the first air passage 23.

The lower side of the internal space S3 of the body 21 is open toward the bottle 11, and the open portion is provided with a valve 26. The valve 26 has a hollow and capped shape made of an elastic body such as silicon rubber, elastomer, and natural rubber and has a slit 26a at its tip end. The slit 26a is closed when the pressure inside the communicating part S4 is made negative and open when released from a negative pressure. Thus, breast milk is attracted into the internal space S3 when the pressure inside the communicating part S4 is made negative. When the negative pressure is released, the slit 26a is opened to allow the breast milk inside the internal space S3 to fall into the bottle 11.

In addition, the body 21 includes an attachment/detachment part 25 that is attached to and detached from the bottle 11. The attachment/detachment part 25 shown in FIG. 2 has a dome shape or a cylindrical shape that has space S6 communicating with the internal space S3 therein when the slit 26a of the valve 26 is opened. Further, the attachment/detachment part 25 includes a female screw part 25a (not shown in FIG. 1) therein, and the female screw part 25a is threadedly engaged with a male screw part (not shown) formed on the periphery of the mouth of the bottle 11 in FIG. 1. Note that the bottle 11 may be a dedicated article for the breast pump 20, a baby bottle or the like adapted to the attachment/detachment part 25, or a bag instead of a molded container. In the present embodiment, the attachment/detachment part 25 has the opening part 28 corresponding to the mouth of a baby bottle so that not only a dedicated article for the breast pump 20 but also the prescribed baby bottle is configured to be attachable/detachable.

In addition, the body 21 has, at its upper part and position opposite to the hood 16, an arm 48 that extends so as to be on the upper side of the base part 41 to which the diaphragm 30 is connected. Preferably, the arm 48 is positioned at a place adjacent to the diaphragm 30 and exceeding the upper end of the diaphragm 30. Further, the arm 48 has, at its upper end, a support shaft part 49 for attaching the handle 61.

Figure 4:
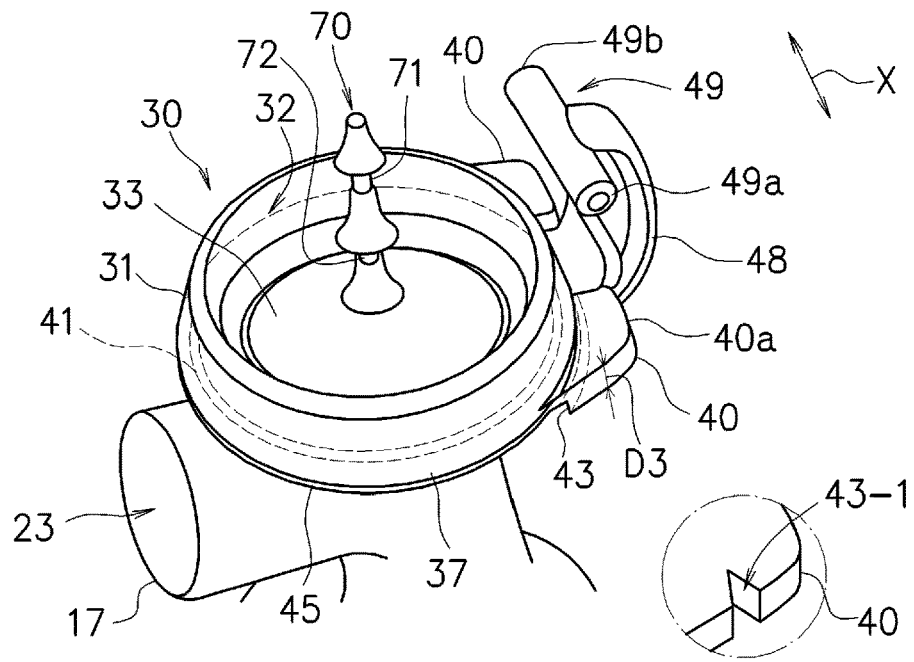
FIG. 4 is a partial perspective view of the diaphragm and the vicinity of a support shaft part when visually recognized from their upper sides, with the hood and the handle of the manual breast pump according to the first embodiment of the present invention removed.

FIG. 4 is a partial perspective view of the support shaft part 49 and the vicinity of the diaphragm 30 when visually recognized from their upper sides. As shown in FIGS. 4 and 1, the support shaft part 49 extends from the arm 48 along a width direction X of the handle 61, and both ends 49a and 49b are attachably/detachably connected to a pair of bearing parts 64 in the width direction X inside the handle 61. Thus, the handle 61 is rotatable around the support shaft part 49 (a Y-direction in FIG. 2) about the support shaft part 49 of the body 21. Note that the present invention is not limited to such a mode. It may be possible to form the bearing parts 64 into round through-holes and insert the support shaft part 49 into the through-holes to make the bearing part 64 and the support shaft part 49 not attachable/detachable to/from each other.

The body 21 has a size at which a user is allowed to grasp the body 21 with one hand. As shown in FIG. 2, the body 21 has, at its outer peripheral lateral surface on the side of the hood 16, a curved recessed part 19 to which a thumb TB is allowed to easily adhere. Then, the user grasps the body 21 and the lever part 61B with one hand at the same time by making any finger FG other than the thumb contact a lever part 61B of the handle 61 with the thumb TB put on the recessed part 19, and grasps or releases the hand to allow the rotating operation of the handle 61 about the support shaft part 49.

[Diaphragm]

The diaphragm 30 is a negative-pressure generating member for generating a negative pressure. In the present embodiment, the diaphragm 30 is connected to the base part 41 of the body 21 so as to be coated on the communicating part S4 in use.

As shown in FIGS. 2 and 4, the diaphragm 30 is a sheet-shaped stuff intricately folded and formed into a shape similar to a bottomed cylindrical body that is totally relatively flat. Specifically, the diaphragm 30 has a first wall part 31 that rises on an outside and has such rigidity as to maintain its outer diameter and a second wall part 32 that is integrally folded back inward at its upper end and makes its portion ahead of the folded-back portion thinner than the first wall part 31. The second wall part 32 is a deformation part and has, at its lower end, a bottom surface part 33 that serves as a relatively wide inside bottom part provided to be integrally extended so as to seal the lower part of a cylindrical shape.

That is, the first wall part 31 and the second wall part 32 are made of the same material but caused to have different rigidity in such a manner that the thickness of the material is made different. Therefore, when an external force by the operation of the handle acts, the second wall part 32 can deform even if the external force is at a level at which the first wall part 31 does not deform.

Figure 3:
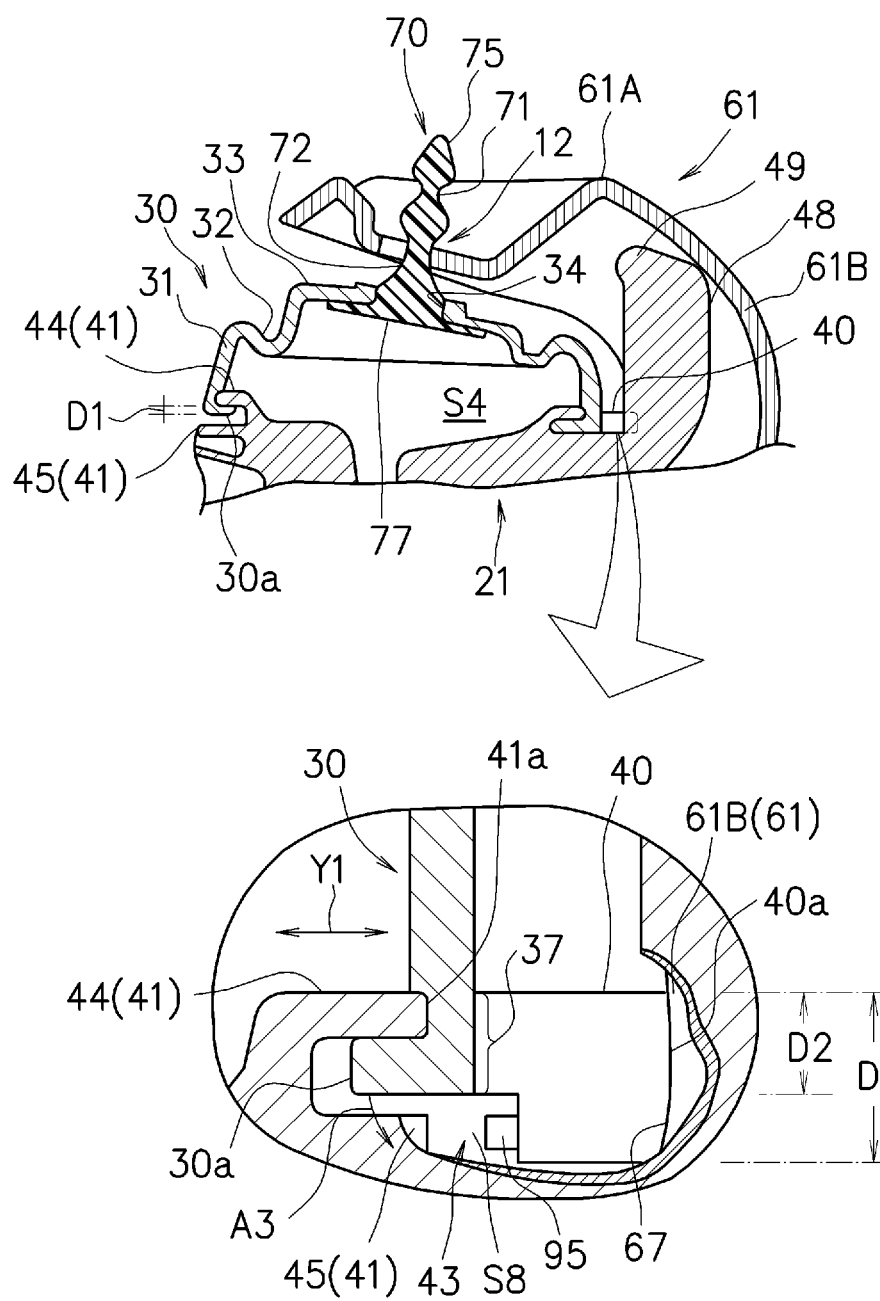
FIG. 3 is a central longitudinal cross-sectional view in the vicinity of a diaphragm deformed by the operation of a handle in FIG. 2 (a view surrounded by dashed lines is an enlarged view in the vicinity of a colliding part).

Thus, as shown in FIG. 3, the diaphragm 30 applies a certain amount of a negative pressure in such a manner that the second wall part 32 serving as a deformation part deforms with the operation of the handle 61 and the space of the communicating part S4 formed between the bottom surface part 33 and the base part 41 changes its capacity. Then, when the pressure inside the space of the communicating part S4 becomes negative, the diaphragm 30 can attract air inside the first air passage 23 via the second air passage 27 and the internal space S3 shown in FIG. 2 and suck breast milk. On this occasion, the first wall part 31 deforms very little, so that the diaphragm 30 can maintain its connected state with respect to the base part 41.

Note that in the present embodiment, even if the base part 41 does not have a height as high as its left side as shown in FIG. 2, the diaphragm 30 has the rising first wall part 31. Therefore, the diaphragm 30 substantially deforms above the base part 41 to allow the generation of a desired negative pressure in the communicating part S4. However, the present invention is not limited to such a mode. For example, in a case in which the base part 41 has a cylindrical shape or a cup shape having a wall part with a substantial height to surround the periphery of the communicating part S4, the diaphragm may be connected so as to cover the upper opening part of the cylindrical shape or the cup shape and formed into a shape recessed toward the inside of the cylindrical shape or the cup shape. Thus, the diaphragm may be configured to be deformable inside the cylindrical shape or the cup shape. In addition, the diaphragm 30 of the present invention is not limited to an attachable/detachable type but may be fixed to the base part 41.

In the present embodiment, the diaphragm 30 is provided with a bonding part 70 that is connected to the handle 61 and used to deform the second wall part 32. The bonding part 70 is made of a rigid material that is more rigid compared with the second wall part 32 serving as a deformation part and totally made of, for example, a synthetic resin such as polypropylene, polycarbonate, polycycloolefin, and polyethersulfone.

The bonding part 70 has a low and flat disc-shaped base part 77 formed by widely expanding the radius of its base end, and the base part 77 is arranged on the lower side (on the side of the communicating part S4) of the bottom surface part 33.

In addition, the bonding part 70 has a connecting part 75 that protrudes upward from the base part 77 and extends like a shaft, and that is used to be connected to the handle 61. The connecting part 75 is connectable to the handle 61 when inserted into a through-hole (a hole having a radius smaller than that of the base part 77) 34 formed at the central part of the bottom surface part 33 and exposed to the upper side of the bottom surface part 33. Thus, when the connecting part 75 is pulled up by the handle 61, the base part 77 pushes up the bottom surface part 33 and the second wall part 32 greatly deforms the space of the communicating part S4. Note that the base part 77 of the present embodiment is arranged on the lower side of the bottom surface part 33 without being connected to the bottom surface part 33, but the present invention is not limited to this. For example, the base part 77 may be fixed to the upper side of the bottom surface part 33.

Further, the connecting part 75 has a plurality of engaging parts 71 and 72 in its extending direction (a substantially vertical direction in the figures) Z, and thus a connected position in the extending direction Z between the handle 61 and the connecting part 75 can be changed. Accordingly, the deformation amount of the diaphragm 30 can be changed with a change in a distance at which the connecting part 75 is pulled up by the handle 61. The engaging parts 71 and 72 may have any configuration so long as the engaging parts 71 and 72 are allowed to engage the handle 61 by changing their positions. However, in the present embodiment, the engaging parts 71 and 72 are a plurality of groove-shaped parts formed stepwise in the extending direction Z. By the engagement between the groove-shaped parts and the handle 61, the distance at which the connecting part 75 is pulled up by the handle 61 can be changed stepwise.

The diaphragm 30 is integrally made of a flexible deformation material totally relatively rich in elasticity, that is, a synthetic resin having a hardness HS of 30 to 70 measured by an A-type durometer according to JIS-K6253 (ISO7619), for example, silicon rubber, isoprene rubber, elastomer such as SEBS (styrene-ethylene-butylene-styrene), or the like.

Silicon rubber is used in the diaphragm 30 of the present embodiment, and a material constituting the portion of the first wall part 31 preferably has a thickness of 1.5 mm to 3.0 mm. This is because the first wall part 31 is buckled during the generation of a negative pressure when the thickness of the first wall part 31 is smaller than 1.5 mm and the first wall part 31 is less liable to deform and thus is not easily attached to the base part 41 of the body 21 when the thickness of the first wall part 31 exceeds 3.0 mm.

Specifically, the first wall part 31 of the diaphragm 30 is extended downward, and its lower end 30a is folded inward. The folded lower end 30a also has a thickness D1 of 1.5 mm to 3.0 mm. Further, when the diaphragm 30 is connected to the base part 41, the lower end 30a is accommodated in the outer groove 46 ahead of the first flange 44 while the diaphragm 30 is caused to deform with the first wall part 31 subjected to slight stretching or the like.

[Handle]

Figure 5:
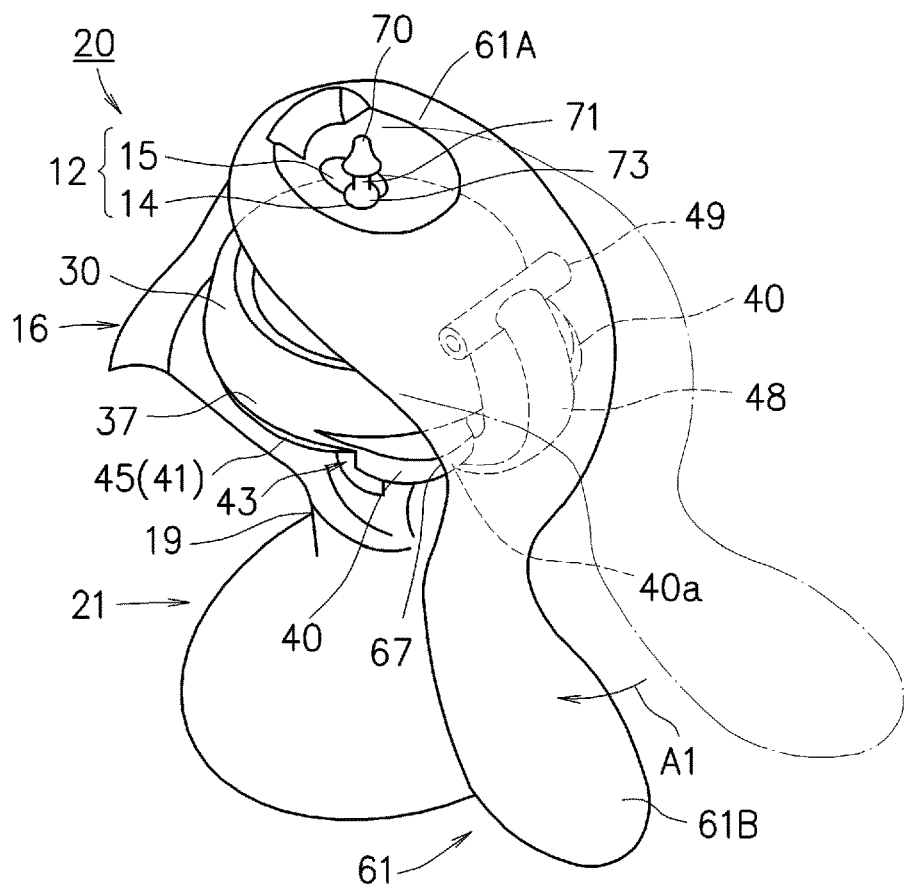
FIG. 5 is a view of a use state in which the handle of the manual breast pump according to the first embodiment of the present invention is rotated.

The handle 61 will be described with reference to FIGS. 1, 2, and 5. FIG. 5 is a view showing a state in which the handle 61 of the breast pump 20 approaches the body 21.

As shown in the figures, the handle 61 has a long shape, is totally relatively rigid, and is integrally made of a light synthetic resin. The handle 61 is a molded article made of, for example, polypropylene, polycarbonate, polycycloolefin, polyethersulfone, or the like.

The handle 61 has a lift part 61A that is arranged above the diaphragm 30 and lifts up the diaphragm 30 and has a lever part 61B that is folded from the lift part 61A and positioned corresponding to the lateral surface of the body 21.

The lift part 61A is provided with a connected part 12 connected to the connecting part 75. The connected part 12 in the figures has a holding opening part 14 that is used to hold a position connected to the connecting part 75 and an insertion opening part 15 that is a hole connected to the holding opening part 14 and used to insert the connecting part 75. The holding opening part 14 is slightly greater than the outer peripheries of the engaging parts 71 and 72 but has an opening area smaller than the outer diameters of portions 73 adjacent to the engaging parts 71 and 72 of the connecting part 75. On the other hand, the insertion opening part 15 has an opening area greater than the outer diameters of the adjacent portions 73. Thus, the connecting part 75 is inserted into the insertion opening part 15 and then slid to place the engaging parts 71 and 72 in the holding opening part 14, whereby the handle 61 and the connecting part 75 can be positioned and connected to each other.

The lever part 61B has a lever shape and serves as a handle. As described above, a user puts her fingers FG other than a thumb on the outside surface of the lever part 61B. A distance W1 between the outside surface on which the fingers FG are put and the recessed part 19 on which the thumb TB is put is a distance at which the body 21 can be sandwiched and grasped between the outside surface and the recessed part 19. Then, when the grasped hand is held, the lever part 61B is pressed in an A1 direction in FIGS. 2 and 5 and approaches the body 21. When the handle 61 rotates about the support shaft part 49, the lift part 61A lifts up the diaphragm 30 via the bonding part 70 as shown in FIG. 3. Thus, the space of the communicating part S4 increases, and the pressure inside the space becomes negative. As a result, breast milk is sucked. On the other hand, when the hand is released or a grasping force is weakened, the elastic force of the diaphragm 30 acts. Thus, the diaphragm 30 returns to its original state in FIG. 2 in which an external force has not been applied, and the lever part 61B also separates from the body 21 and returns to its original position. As a result, the negative-pressure state of the communicating part S4 is cancelled, and the valve 26 is opened. As a result, the sucked breast milk falls. As described above, the diaphragm 30 deforms when the handle 61 rotates so as to make the lever part 61B approach and separate from the body 21.

In addition, the lever part 61B is curved so as to be gradually directed outward toward a lower side from a region in which the fingers FG are put. Thus, a lower end 63 shows an external appearance slightly flipping up outward, and the fingers FG are hardly deviated downward when the lever part 61B approaches the body 21.

Moreover, such a handle 61 for operation that is designed for manually expressing milk is curved to have a cavity part S7 opened toward the side of the body 21. The cavity part S7 of the present embodiment is used to hide a connection mechanism part between the body 21 and the handle 61 such as the support shaft part 49 and a rib 39 to obtain a preferable design.

[Quietness Mechanism (Colliding Part)]

The breast pump 20 of the present embodiment has the above characteristics and further has a quietness mechanism. Hereinafter, the characteristic quietness mechanism will be described.

According to the present invention, a colliding part 40 against which at least the lever part 61B and the body 21 collide before directly contacting each other (in the present embodiment, the colliding part 40, against which the handle 61 and the body 21 collide so as not to directly contact each other) when the lever part 61B approaches the body 21, is provided in at least the region of any of the handle 61, the body 21, and the diaphragm 30. That is, the colliding part 40 is interposed between the handle 61 and the body 21 and/or between the handle 61 and the diaphragm 30 and makes a collision during the operation of the handle.

In the present embodiment, the colliding part 40 is provided in the region of the diaphragm 30. Thus, even in a state in which the lever part 61B approaches the body 21 most closely as shown in FIG. 2 by dashed lines, space S is generated between the handle 61 and the body 21 to positively prevent the collision between the handle 61 made of a rigid synthetic resin and the body 21 and eliminate a collision sound generated by the collision.

Further, the colliding part 40 is integrally made of the same material as that of a region in which the colliding part 40 is arranged, and has a damper structure that absorbs an impulsive force or reduces the propagation of the impulsive force during a collision. In the figures, the colliding part 40 is arranged in the region of the diaphragm 30. Therefore, the colliding part 40 is made of a flexible deformation material relatively rich in elasticity same as that of the diaphragm 30 (for example, silicon rubber, isoprene rubber, or elastomer, silicon rubber in the present embodiment). Accordingly, when the lever part 61B approaches the body 21 and collides against the colliding part 40, the colliding part 40 exhibits an excellent function as a damper structure due to its deformation easiness and can effectively absorbs an impulsive force or reduce the propagation of the impulsive force. In addition, since the colliding part 40 is integrally formed with the diaphragm 30, the colliding part 40 can be prevented from coming off the diaphragm 30 as much as possible even if the colliding part 40 repeatedly collides against the handle 61.

In this regard, attention should be paid to the fact that the diaphragm 30 is a pump that applies a negative pressure through its deformation, and that the colliding part 40 formed to protrude from the diaphragm 30 adversely effects the pump function, which gives rise to a problem occurring when the diaphragm 30 and the colliding part 40 are integrally formed with each other. Therefore, in order to solve the problem, the present embodiment has the following various configurations.

First, as shown in FIGS. 3 to 5, the colliding part 40 protrudes from a connecting region 37 of the diaphragm 30, the connecting region 37 being connected to the base part 41, so as to be capable of colliding against the handle 61. Thus, the connecting region 37 of the diaphragm 30, the connecting region 37 being connected to the base part 41, is present in a direction in which an impulsive force generated when the colliding part 40 makes a collision is transmitted, and the impulsive force acts on the connecting region 37 via the colliding part 40 (transmitted toward the connecting region 37). The first and second wall parts 31 and 32 (particularly, the second wall part 32 serving as a deformation part) of the diaphragm 30 are not substantially influenced even if an impulsive force is applied to the connecting region 37. Therefore, an adverse effect on the negative-pressure generating function of the diaphragm 30 can be prevented as much as possible. Note that the protruding colliding part 40 also serves as a knob that is to be used when the base part 41 and the diaphragm 30 are attached to and detached from each other.

Next, the colliding part 40 has a fragile part 43 at its root (on the side of the base part 41) or halfway point in a protruding direction Y1. The fragile part 43 of the present embodiment is a notched part which is notched in a thickness direction along the outer periphery of the base part 41 and in which a root-side thickness D2 is relatively smaller than a tip end side thickness D3 (in the figure, D2 is about 2 mm that is half or less of the thickness of D3, about 5 mm). Accordingly, stress generated when the handle 61 makes a collision is focused on the fragile part 43. Therefore, an adverse effect on the negative-pressure generation portion of the diaphragm 30 can be effectively prevented.

As shown in FIGS. 1 and 3, the fragile part 43 serving as the notched part is notched from its lower side. This is because if the fragile part 43 is notched from an upper side, the colliding part 40 is folded to its upper side based on the fragile part 43 (the lower end 30a locked in the lower surface of the base part 41 is folded in an A3 direction in which the locking is released in FIG. 3) when the handle 61 makes a collision, which results in a cause for an accident in which the diaphragm 30 comes off the base part 41.

In addition, the fragile part 43 is formed on the side of the base part 41 so that the colliding part 40 exhibiting also a knobbing function to remove diaphragm 30 as described above is easily knobbed.

Moreover, the fragile part 43 of the present embodiment partially has, on its notched inside surface, a convex part 95 that faces the base part 41 (the second flange 45 that is the portion of the base part 41 in the figures). Space S8 is provided between the tip end surface of the convex part 95 and the base part 41. Thus, the colliding part 40 can be prevented from being excessively folded to its lower side (in the A2 direction of FIG. 1), while the fragile part 43 having a certain size is formed. Accordingly, a user is prevented from performing a handling operation in which the colliding part 40 is uselessly pressed (that is, the user presses the colliding part 40 more than necessary although the diaphragm 30 has substantially deformed). Thus, the labor of the user can be alleviated.

Note that the fragile part 43 of the present invention is not limited to a notched part but may be a concave part. In addition, the fragile part 43 notched from the lower side along the outer periphery of the base part 41 is described here as a preferred embodiment. However, as shown in a view surrounded by dashed lines in FIG. 4, a notched part 43-1 may be formed on a protruding halfway point lateral surface.

Next, as shown in FIG. 3, the colliding part 40 protrudes substantially along the direction Y1 in which the base part 41 extends from a position corresponding to a tip end surface 41a (a tip end surface of the first flange 44) of the base part 41, and the handle 61 collides against the tip end surface 40a of the colliding part 40 substantially along the direction Y1 in which the base part 41 extends. Accordingly, since the colliding part 40 against which the handle 61 collides contracts toward the tip end surface 41a of the base part 41, the deformation function of the diaphragm 30 is hardly influenced. Note that the tip end surface 41a of the base part 41, the tip end surface 40a of the colliding part 40, and a colliding end surface 67 of the handle 61 are substantially parallel to each other when the handle 61 that makes a collision collides against the colliding part 40.

As shown in FIGS. 4 and 5, the colliding part 40 includes a pair of colliding parts 40 and protrudes in a tongue shape toward both sides of an arm 48 so as to detour around the arm 48 extending from the body 21 (the colliding part 40 protrudes substantially horizontally in the figures). Further, the pair of colliding parts 40 is capable of colliding against both ends 67 in the width direction X close to the body 21 in the curved lever part 61B of the handle 61 shown in FIG. 1. Note that the colliding part 40 is capable of colliding against the handle 61 regardless of which of the plurality of engaging parts 71 and 72 shown in FIG. 2 engages the handle 61. In addition, the pair of colliding parts 40 has the same configuration.

First Modified Example of First Embodiment

Figure 6:
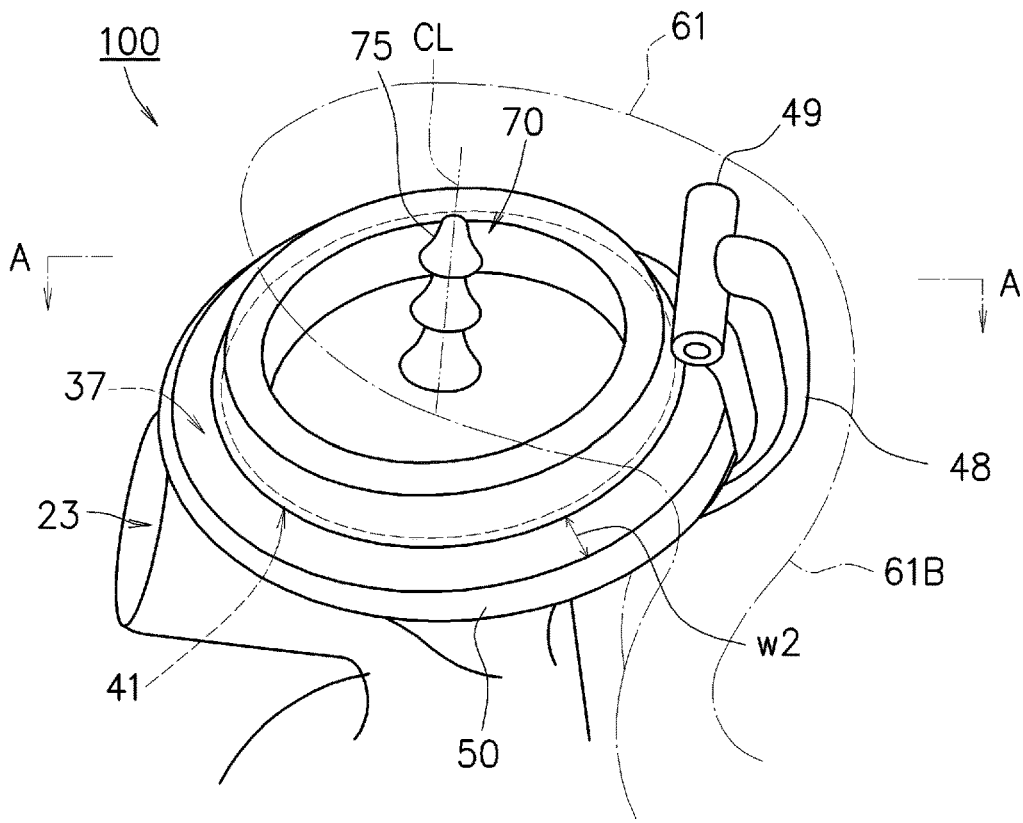
FIG. 6 shows a first modified example of the first embodiment of the present invention and is a partial perspective view of the vicinity of the deformed diaphragm when visually recognized from its upper side.
Figure 7:
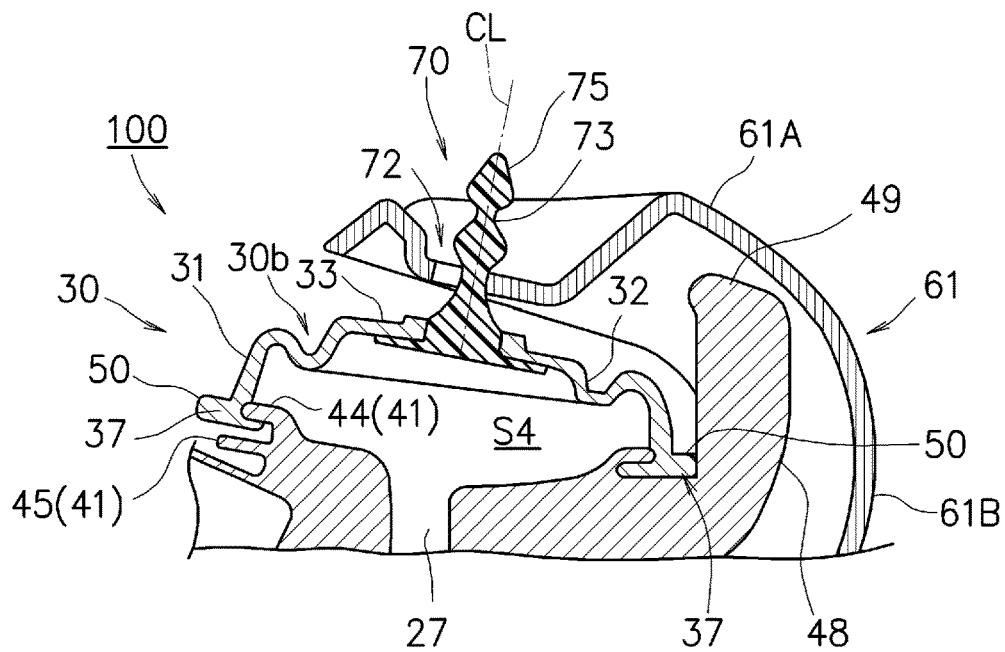
FIG. 7 is an A-A cross-sectional view of FIG. 6.

FIGS. 6 and 7 show a breast pump 100 according to a first modified example of the first embodiment of the present invention. FIG. 6 is a partial perspective view of the vicinity of a diaphragm 30 when visually recognized from its upper side, and FIG. 7 is an A-A cross-sectional view of FIG. 6. Note that FIG. 6 shows a state in which the diaphragm 30 is pulled up by a handle 61 when a user grasps her hand. In addition, the handle 61 shown in FIG. 6 is transparent.

In the figures, parts denoted by the same symbols as those of the breast pump 20 in FIGS. 1 to 5 have the same configurations, and thus their duplicated descriptions will be omitted. Hereinafter, a different point will be mainly described.

The breast pump 100 according to the present modified example is different from the above embodiment only in the configuration of a colliding part 50.

That is, the colliding part 50 of the present modified example protrudes from the circumference of a connecting region 37 surrounding a base part 41. Specifically, the base part 41 totally has a flange shape in the same manner as in the above first embodiment, and the diaphragm 30 has the ring-shaped connecting region 37 connected so as to cover the circumference of the flange-shaped part. Further, the colliding part 50 protrudes from the circumference of the connecting region 37 and has a ring shape.

The flange-shaped base part 41, the ring-shaped connecting region 37, and the ring-shaped colliding part 50 are preferably concentric about a central axis CL of the connecting part 75 in a plan view, and a protruding width W2 of the colliding part 50 is the same in any position. Note that the colliding part 50 of the present invention is not limited to the above mode but the width W2 may be changed according to a position.

The first modified example of the first embodiment of the present invention is configured as described above. Accordingly, the service life of the diaphragm 30 can be extended. That is, as shown in FIG. 7, a support shaft part 49 that pivotally supports the handle 61 is placed at a position different from the position of a central axis CL (that is the same as the central axis of the connecting part 75) of the diaphragm 30, and the handle 61 is pivotally supported on one side. Therefore, when the handle 61 is rotated, the diaphragm 30 is greatly lifted up at a portion 30b on its side opposite to the side of the support shaft part 49 compared with the side of the support shaft part 49. For this reason, the portion 30b is liable to be degraded first. In order to address the problem, the greatly-lifted portion can be changed by the rotation of the diaphragm 30 including the colliding part 50 at any timing, and thus the service life of the diaphragm 30 can be extended. Further, since the colliding part 50 is arranged so as to surround the circumference of the base part 41 even when the diaphragm 30 including the colliding part 50 is rotated, the colliding part 50 and the handle 61 can collide against each other.

Second Modified Example of First Embodiment

Figure 8:
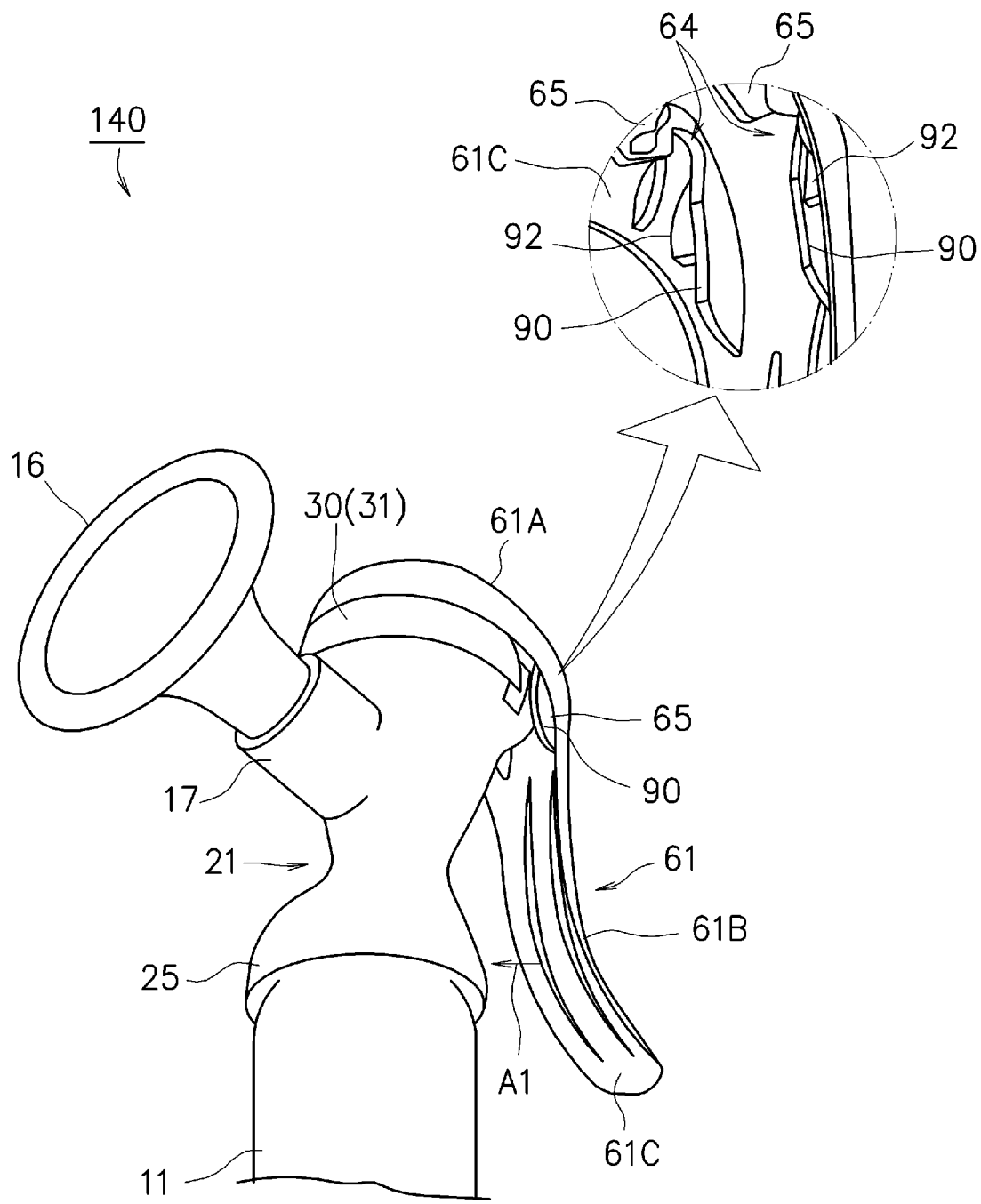
FIG. 8 is a schematic perspective view of a manual breast pump according to a second modified example of the first embodiment of the present invention.
Figure 9:
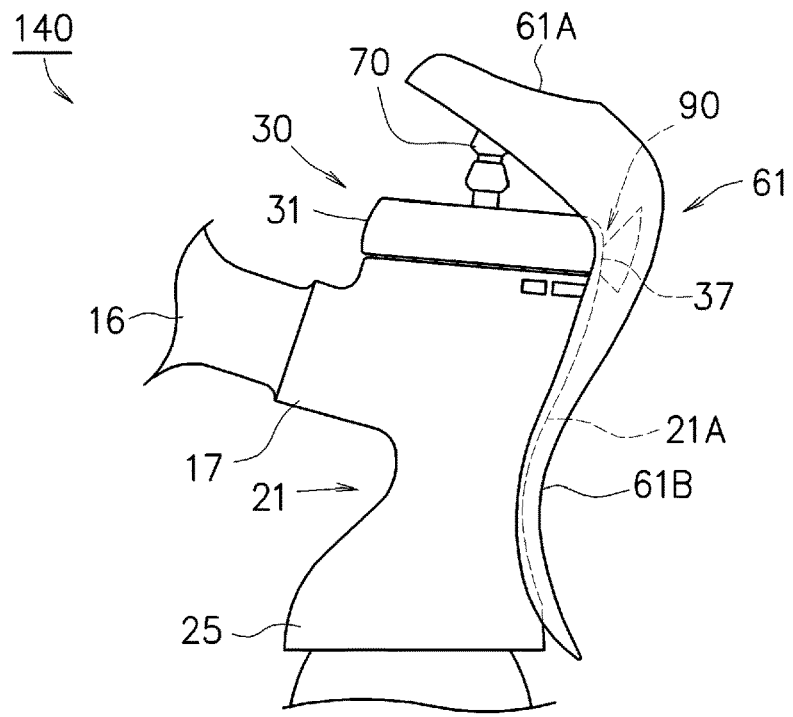
FIG. 9 is a schematic front view of the manual breast pump in a state in which a handle in FIG. 8 approaches a body most closely.
Figure 10:
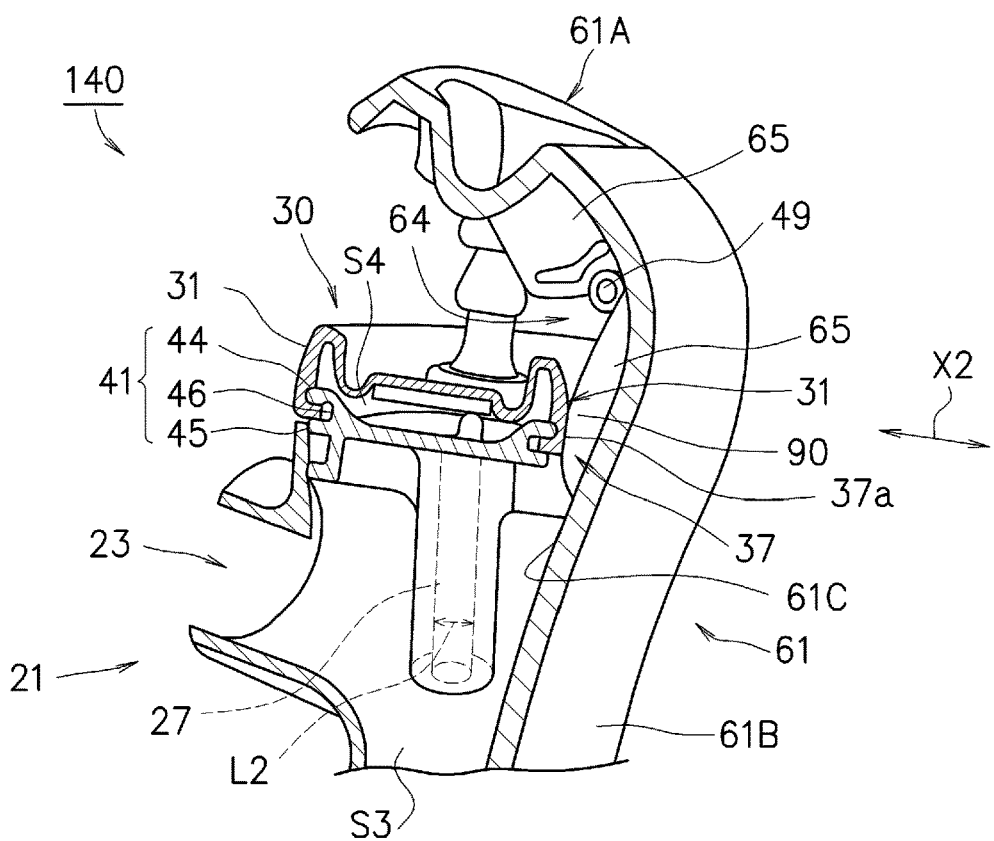
FIG. 10 is a schematic longitudinal cross-sectional view of the manual breast pump in FIG. 9 in a case in which the breast pump is vertically cut off in the vicinity of a colliding part.

FIGS. 8 to 10 show a breast pump 140 according to a second modified example of the first embodiment of the present invention. FIG. 8 is a schematic perspective view of the breast pump 140, FIG. 9 is a schematic front view thereof in a state in which a handle 61 approaches a body 21 most closely, and FIG. 10 is a schematic longitudinal cross-sectional view thereof in a case in which the breast pump 140 in FIG. 9 is vertically cut off in the vicinity of a colliding part 90. Note that a view surrounded by dashed lines in FIG. 8 is an enlarged view in which the inside surface of the handle 61 in the vicinity of the colliding part 90 is enlarged. In addition, a hood is omitted in FIG. 10.

In the figures, parts denoted by the same symbols as those of the breast pumps 20 in FIGS. 1 to 7 have the same configurations, and thus their duplicated descriptions will be omitted. Hereinafter, a different point will be mainly described.

In the second modified example, a damper structure using the deformation easiness (impact absorption) of the diaphragm 30 is a quietness mechanism in the same manner as in the first embodiment. However, the damper structure is not formed in the colliding part 90 but is formed in a collided part.

That is, the colliding part 90 against which the handle 61 and the body 21 collide before directly contacting each other is provided in the region of the lever part 61B that is close (preferably closest) to the diaphragm 30 when the lever part 61B is operated to approach the body 21. In this case, the region of the diaphragm 30 against which the colliding part 90 collides serves as the collided part.

Specifically, the diaphragm 30 of the present second modified example does not have a shape protruding from a connecting region 37 as shown in FIG. 4 but has the same shape as that of a conventional type. As shown in FIG. 10, the diaphragm 30 has a shape similar to a bottomed cylindrical body that is totally relatively flat, and includes the connecting region 37 connected to a base part 41 of the body 21 and a first wall part 31 that rises from the connecting region 37 and has such rigidity as to maintain its outer diameter.

Further, the colliding part 90 provided at the handle 61 collides against the connecting region 37 of the diaphragm 30, the connecting region 37 being connected to the base part 41. Accordingly, even if the colliding part 90 is integrally made of the same material as that of the handle 61 and relatively rigid, the connecting region 37 absorbs an impulsive force to makes it possible to achieve quietness. In addition, an impulsive force generated when the colliding part 90 makes a collision acts on the connecting region 37 of the diaphragm 30, the connecting region being connected to the base part 41. Thus, an adverse effect on the negative-pressure generating function of the diaphragm 30 is prevented to a greater extent.

Note that the whole collided part against which the colliding part 90 collides is preferably the connecting region of the diaphragm 30 but the present invention is not limited to the mode. It is sufficient that at least a part of the collided part serves as the connecting region 37 of the diaphragm 30. That is, as shown in FIG. 10, the colliding part 90 may abut against a portion other than the connecting region 37 of the diaphragm 30 so long as the colliding part 90 abuts against the connecting region 37. Thus, a part of the colliding part 90 abuts against the connecting region 37, and the colliding part 90 cannot greatly advance any more toward the side of the base part 41. Accordingly, even if the colliding part 90 abuts against the diaphragm 30 at a portion other than the connecting region 37, an influence on the negative-pressure generating function of the diaphragm 30 is small.

In the present embodiment, the colliding part 90 is formed to collide against the connecting region 37 and the first wall part 31 at substantially the same time. As described above, the first wall part 31 has such rigidity as to maintain its outer shape. In this sense as well, an influence on the negative-pressure generating function of the diaphragm 30 is small.

Here, the colliding part 90 collides against a surface (that is, an expanding surface of the connecting region 37) 37a in the thickness direction (an X2 direction in FIG. 10) of the connecting region 37 serving as the collided part. Thus, the collided part is hardly folded even if the colliding part 90 makes a collision. That is, for example, the colliding part 40 shown in FIG. 4 protrudes in the tongue shape from the connecting region 37. When the handle 61 collides against the end surface of the colliding part 40 and is further deeply grasped, there is a likelihood that the collided part is folded to cause a handling operation with a sense of discomfort. However, when the colliding part 90 collides against the surface 37a in the thickness direction of the connecting region 37 as shown in FIG. 10, the collided region is prevented from being folded and thus the handle 61 can smoothly approach the body 21. Accordingly, the stress of a user is prevented, and the expressing of milk is facilitated.

The colliding part 90 is provided on an inside surface 61C of the handle 61 and protrudes in a direction in which the handle 61 approaches and separates from the connecting region 37. The colliding part 90 is integrally made of the same rigid material as that of the handle 61. The colliding part 90 shown in the figures is formed in such a manner that a region (a region on the lower side of a bearing part 64) adjacent to the connecting region 37 of the diaphragm 30 in a bearing member 65 used for forming the notched bearing part 64 (a portion connected to a support shaft part 49 extending from the body 21) is extended. The direction of the extension is a direction in which a rotated lever part 61B approaches the diaphragm 30. Note that the colliding part 90 has a plate shape as shown in FIGS. 8 and 10. In order to prevent deflection during a collision, the colliding part 90 is provided with a reinforcing member 92 for connecting the colliding part 90 and the inside surface 61C of the handle 61 to each other along a direction in which the bearing member 65 is orthogonal to the direction of the extension. As described above, the deflection of the colliding part 90 is also prevented during a handling operation, whereby the handle 61 can smoothly approach the body 21.

Meanwhile, in the present invention, it is sufficient that the colliding part 90 and the connecting region 37 (the collided part) of the diaphragm 30 collide against each other before at least the handle 61 and the body 21 directly contact each other, whereby the collision between the handle 61 and the body 21 is lessened to makes it possible to achieve quietness.

In the present modified example, the lever part 61B shown in FIG. 8 is formed to be thinner than the lever part 61B shown in FIGS. 1 to 7 to exhibit a slight elastic force in a direction A1 in which the lever part 61B approaches the body 21 (the rib shape of the inside surface 61C of the lever part 61B may be devised to exhibit the elastic force). In addition, as shown in FIG. 9, a surface 21A of the body 21 is curved on the side of the handle 61 so as to correspond to the shape of the inside surface of the lever part 61B. Thus, when the lever part 61B approaches the body 21, the colliding part 90 and the diaphragm 30 (the connecting region 37 and the first wall part 31 in the figures) first collide against each other to reduce a colliding force. Then, when a user further strongly grasps the lever part 61B, the lever part 61B is allowed to contact the body 21 while exhibiting an elastic force. Accordingly, the user makes the lever part 61B contact the body 21 by strongly grasping the lever part 61B and can have a sense of fulfillment in that he/she has grasped the lever part 61B to the end. Note that the lever part 61B may not totally contact the body 21 but may partially contact the same. In addition, the lever part 61B may abut against the lower part of the body 21 after abutting against the upper part thereof, or may abut against the upper part after abutting against the lower part.

Moreover, the present modified example is so structured that the movement speed of the handle 61 itself (the speed of the handle 61 at which the handle 61 approaches the body 21) is reduced to lessen the impact between the handle 61 and the body 21 during a collision. That is, as shown in FIG. 10, a second air passage 27 close to a communicating part S4 among a plurality of air passages (first and second air passages) 23 and 27 that connects the communicating part S4 that is space covered by the diaphragm 30 and space surrounded by the hood to each other has an inside diameter L2 for reducing the speed in the direction in which the handle 61 approaches the body 21. That is, the second air passage 27 serves not only as a passage for sucking breast milk but also as a speed adjustment passage for adjusting the operation speed of the handle 61. Accordingly, the abutment between the handle 61 and the body 21 is soft when the handle 61 and the body 21 abut against each other, and an excellent quietness function is realized in cooperation with the above damper structure and the elastic force of the lever part 61B.

Note that the inside diameter L2 of the second air passage 27 is the same at any portion in FIG. 10 but the present invention is not limited to such a mode. A constricted part in which the inside diameter of one portion is smaller than the inside diameter of the other portion in a height direction may be formed.

Second Embodiment

Figure 11:
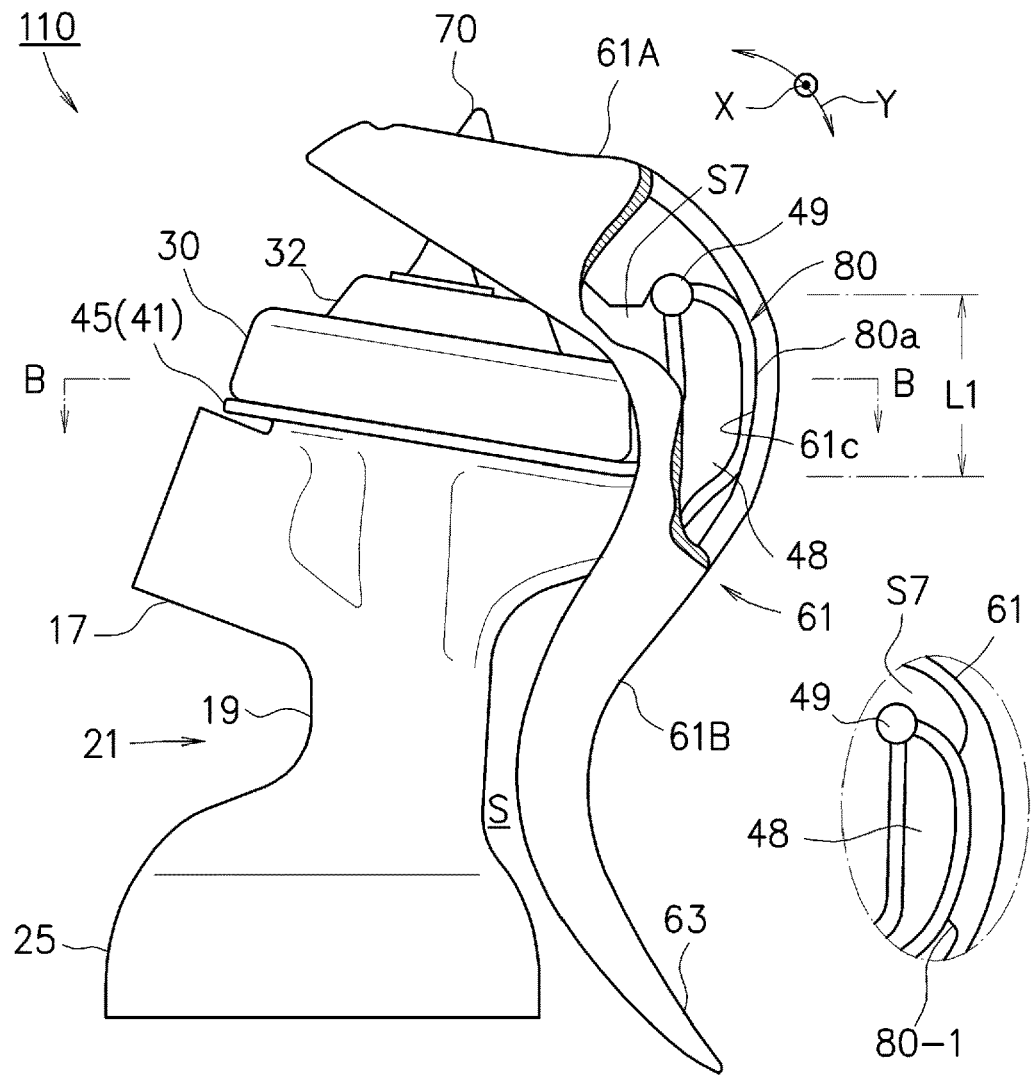
FIG. 11 is a front view of a manual breast pump according to a second embodiment of the present invention.
Figure 12:
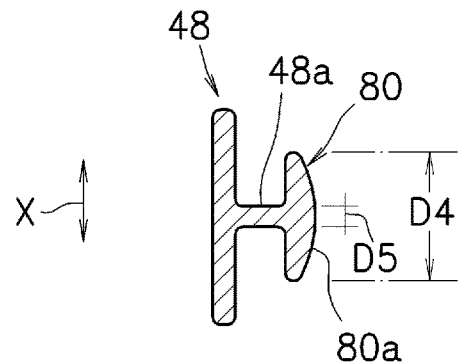
FIG. 12 is a B-B cross-sectional view in the vicinity of a colliding part in FIG. 11.

FIGS. 11 and 12 show a breast pump 110 according to a second embodiment of the present invention. FIG. 11 is a front view of the breast pump 110, and FIG. 12 is a B-B end view in the vicinity of a colliding part 80 in FIG. 11. Note that FIG. 11 shows a state in which a lever part 61B approaches a body 21 most closely, and the inside of a cavity part S7 is visually recognized with a part of a handle 61 notched. In addition, a view surrounded by dashed lines in FIG. 11 is a view in the vicinity of a colliding part 80-1 according to a modified example of the second embodiment.

In the figures, parts denoted by the same symbols as those of the breast pumps 20 and 100 in FIGS. 1 to 7 have the same configurations, and thus their duplicated descriptions will be omitted. Hereinafter, a different point will be mainly described.

The breast pump 110 of the second embodiment is different from the breast pump of the above embodiment in that the breast pump 110 uses a cover structure instead of a damper structure as a quietness mechanism.

That is, the colliding part 80 against which the handle 61 and the body 21 collide before contacting each other is structured to be covered (hereinafter called the "cover structure") via a gap so as not to be exposed to an outside when at least the lever part 61B approaches the body 21 most closely. Thus, the leakage of a collision sound to the outside is prevented to improve quietness.

Specifically, the handle 61 has the cavity part S7 opened toward the side of the body 21 as described in the first embodiment, and the colliding part 80 is arranged inside the cavity part S7 when colliding against at least the handle 61. Accordingly, even when an impact sound generated by the handle 61 and the colliding part 80 is air-propagated, the leakage of the sound to the outside can be prevented. Note that the presence of the gap is preferable since the collision sound immediately leaks to the outside unless the colliding part 80 is covered via the gap (the cavity part S7 in the present embodiment).

In FIG. 11, the colliding part 80 is arranged around a support shaft part 49 of the body 21, and the cavity part S7 corresponding to the support shaft part 49 is formed to have the greatest space volume to further prevent the sound from leaking to the outside.

In addition, the colliding part 80 is provided on the side of the handle 61 with a considerable length L1 from the upper part to the central part of an arm 48 extending from the body 21 for forming the support shaft part 49. The length L1 is about 15% to 30% of the length (a dimension in the longitudinal direction) of the handle 61. Further, the colliding part 80 has a shape in which a surface 80*a* on the side of the handle 61 is adapted to adhere to an inside surface 61*c* of the handle 61 even if the colliding part 80 has the considerable length L1. In the figure, the colliding part 80 has the same curved shape as that of the inside surface 61*c*. In addition, the colliding part 80 extends so as to correspond to the shape of the inside surface 61*c* corresponding to a width direction X (the thickness direction of the breast pump 110) of the handle 61, whereby a thickness D4 of the colliding part 80 is made greater than the thickness D5 of the central part 48*a* of the arm 48. As described above, the colliding part 80 corresponds to the shape of the inside surface 61*c* or extends. Thus, in a range in which the collision sound hardly leaks from the cavity part S7, the colliding part 80 collides against the inside surface 61*c* of the handle 61 in a plane shape as much as possible, and the area of the colliding part 80 contacting the handle 61 is increased.

In addition, as for a collided position, the colliding part 80 is arranged so as to collide against the substantially central part in the width direction X and/or the length direction of the handle 61.

The present second embodiment is configured as described above, but the "cover structure" of the present invention is not limited to the above embodiment. As shown in, for example, a view surrounded by the dashed lines in FIG. 11, the colliding part 80-1 may be arranged in the region of the handle 61. That is, the colliding part 80-1 in the view protrudes from the inside surface of the handle 61, and collides against the arm 48 of the body 21 when the lever part 61B approaches the body 21 most closely. In this regard, compared with the colliding part 80-1 according to the modified example of the second embodiment, the colliding part 80 of the second embodiment collides with the handle 61 at a deeper place of the cavity part S7 and thus has a mode in which the leakage of a collision sound to the outside is further prevented. Therefore, the colliding part 80 is preferable in terms of quietness.

Third Embodiment

Figure 13:
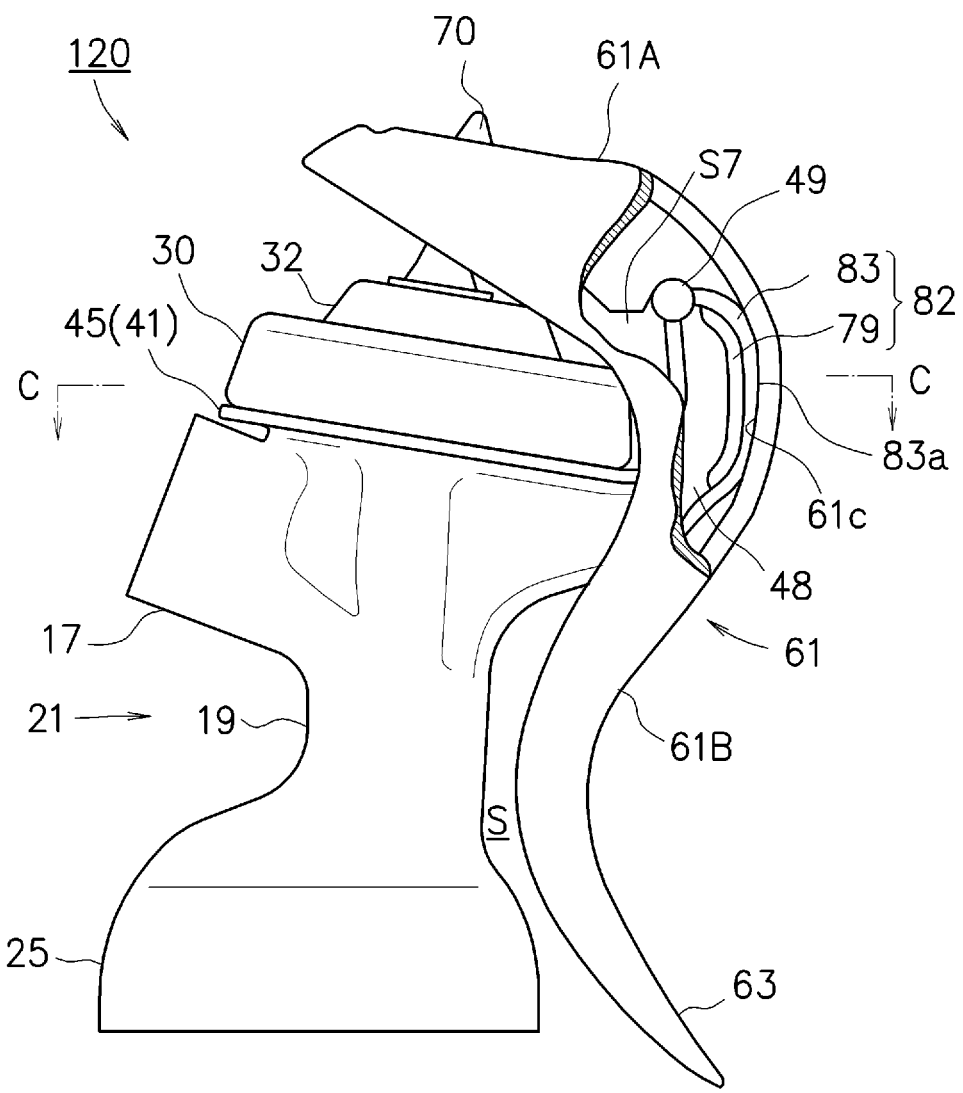
FIG. 13 is a front view of a manual breast pump according to a third embodiment of the present invention.
Figure 14:
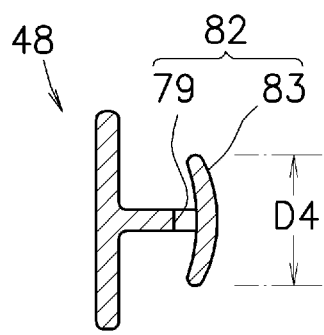
FIG. 14 is a C-C cross-sectional view in the vicinity of a colliding part in FIG. 13.

FIGS. 13 and 14 show a breast pump 120 according to a third embodiment of the present invention. FIG. 13 is a front view of the breast pump 120, and FIG. 14 is a C-C end view in the vicinity of a colliding part 82 in FIG. 13. Note that FIG. 13 shows a state in which a lever part 61B approaches a body 21 most closely and the inside of a cavity part S7 is visually recognized with a part of a handle 61 notched.

In the figures, parts denoted by the same symbols as those of the breast pumps 20, 100, and 110 in FIGS. 1 to 12 have the same configurations, and thus their duplicated descriptions will be omitted. Hereinafter, a different point will be mainly described.

The breast pump 120 of the third embodiment is different from the breast pumps of the above embodiments only in the configuration of the colliding part 82.

That is, the colliding part 82 in FIG. 13 has a cover structure in which the colliding part 82 is covered via a gap so as not to be exposed to an outside similarly to the colliding part 82 in FIG. 11. Besides, the colliding part 82 also has a damper structure with which an impulsive force generated when the colliding part 82 collides against the handle 61 is absorbed or propagated.

Specifically, the colliding part 82 present inside a cavity part S7 at least during a collision has a through-hole 79. Therefore, since stress (impulsive force) generated when the handle 61 collides against the colliding part 82 is easily focused on the periphery of the through-hole 79, a collision sound can be prevented from propagating through a region other than the colliding part 82. In addition, since the collision sound is prevented from propagating through a portion outside the cavity part S7, the effect of the cover structure can be more effectively exhibited. Accordingly, even if the colliding part 82 is integrally formed with an arm 48 of the body 21, the collision sound can be reduced. Note that the through-hole 79 is preferably arranged on a deeper side (on a side opposite to the opening) of the cavity part S7 to a greater extent. Thus, the collision sound is confined inside the cavity part S7, and the leakage of the sound to the outside can be effectively prevented.

In addition, the colliding part 82 has a colliding-side portion 83 relative to the through-hole 79, and the colliding-side portion 83 has a shape deformable toward the side of the through-hole 79 during a collision. In the figures, the colliding-side portion 83 has a thin plate spring shape in its colliding direction to make the deformation easy. Accordingly, even if the colliding part 82 is made of the same high rigidity material as that of the arm 48, the colliding part 82 can effectively absorb an impulsive force with an increase in its deformation amount.

Note that a surface 83*a* of the colliding-side portion 83 on the side of the handle 61 has preferably a curved shape matched so as to adhere to an inside surface 61*c* of the colliding handle 61, and the through-hole 79 has preferably a shape substantially along the colliding inside surface 61*c*.

The present third embodiment is configured as described above, but the combination of the "cover structure" and the "damper structure" of the present invention is not limited to the above embodiment. For example, a through-hole may be formed in the colliding part 80-1 arranged in the region of the handle 61 shown in the view surrounded by the dashed lines in FIG. 11 to form the damper structure.

Fourth Embodiment

Figure 15:
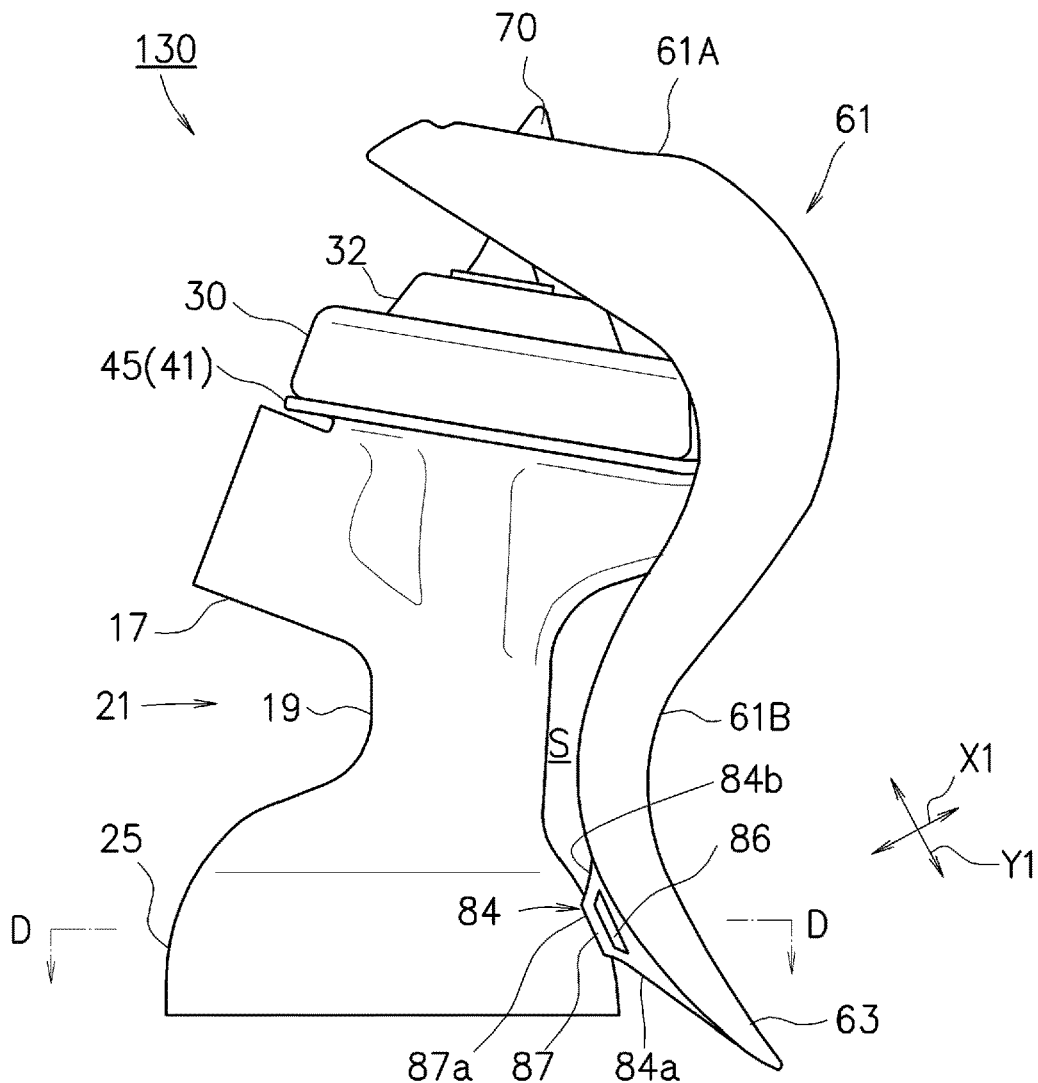
FIG. 15 is a front view of a manual breast pump according to a fourth embodiment of the present invention.
Figure 16:
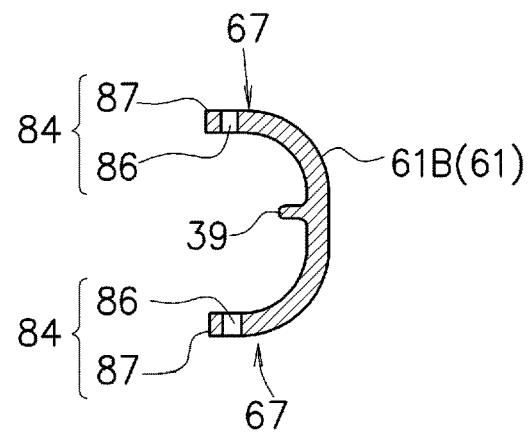
FIG. 16 is a D-D cross-sectional view in the vicinity of a colliding part in FIG. 15.

FIGS. 15 and 16 show a breast pump 130 according to a fourth embodiment of the present invention. FIG. 15 is a front view of the breast pump 130, and FIG. 16 is a D-D end view in the vicinity of a colliding part 84 in FIG. 15.

In the figures, parts denoted by the same symbols as those of the breast pumps 20, 100, 110, and 120 in FIGS. 1 to 14 have the same configurations, and thus their duplicated descriptions will be omitted. Hereinafter, a different point will be mainly described.

The breast pump 130 of the fourth embodiment is different from the breast pumps of the above embodiments only in the configuration of a colliding part 84.

That is, although the colliding part 84 in FIG. 15 has the same damper structure as that of the colliding part 82 in FIG. 13, the colliding part 84 is arranged in a region exposed to the outside of a handle 61 and does not have a cover structure.

Specifically, the colliding part 84 is formed to protrude from positions representing both end surfaces 67 of a lever part 61B of the handle 61 and corresponding to an attachment/detachment part 25 of a bottle toward the side of the attachment/detachment part 25. Further, the colliding part 84 has through-holes 86 halfway through its protruding parts, and colliding-side portions 87 relative to the through-holes 86 are deformable to the side of the through-holes 86 during a collision and have a thin plate spring shape in a colliding direction.

Note that tip end surfaces 87*a* of the colliding-side portions 87 match the shape of the attachment/detachment part 25 and collide against the attachment/detachment part 25 in their plane shapes. In addition, the colliding part 84 in the figures has a width dimension (a dimension in a direction Y1 orthogonal to a protruding direction X1) gradually reducing toward the side of the attachment/detachment part 25 and has inclined surfaces 84*a* and 84*b* in its vertical direction.

The present fourth embodiment is configured as described above. Therefore, the colliding part 84 does not have a cover structure unlike the third embodiment but has the same damper structure as that of the third embodiment. Therefore, since stress (impulsive force) generated when the handle 61 collides against the colliding part 84 is easily focused on the periphery of the through-holes 86, a collision sound can be prevented from propagating through a region (inside a solid object) other than the colliding part 84. In addition, since the colliding-side portions 87 have a plate spring shape deforming to the side of the through-holes 86 during a collision, an impulsive force can be effectively absorbed with an increase in the deformation amount of the colliding part 84.

[Experiments]

A. Experimental Conditions

FIG. 17 shows the types of breast pumps used when noise measurement experiments were conducted. A first type is a conventional breast pump. A second type is also the same as a conventional article, but a body and a handle are molded by a three-dimensional printer. A third type represents the breast pump 110 (see FIG. 11) of the second embodiment in which the body (including the colliding part arranged therein) and the handle are molded by the three-dimensional printer and the diaphragm is made of silicon rubber. A fourth type represents the breast pump 120 (see FIG. 13) of the third embodiment in which the body (including the colliding part arranged therein) and the handle are molded by the three-dimensional printer and the diaphragm is made of silicon rubber. A fifth type represents the breast pump 130 (see FIG. 15) of the fourth embodiment in which the body (including the colliding part arranged therein) and the handle are molded by the three-dimensional printer and the diaphragm is made of silicon rubber. Sixth and seventh types represent the breast pumps 20 (see FIGS. 1 to 5) of the first embodiment. However, the body and the handle of the sixth type are molded by the three-dimensional printer, while the body and the handle of the seventh type are conventional molded articles. Note that the above three-dimensional printer performs molding using an ultraviolet-ray curable resin.

Besides, the experiments were conducted under the following conditions.

Measurement environment: a soundproof shielding room at Tokyo Metropolitan Industrial Technology Research Institute Measurement equipment: SA-A1 manufactured by Rion Co., Ltd. or the like Measurement position: a microphone was installed at a position right above a breast pump by 20 cm Measurement method: the operation of grasping a handle once every second was repeatedly performed for ten seconds, and a maximum sound pressure level during the period was recorded.

B. Experimental Results

Figure 19:
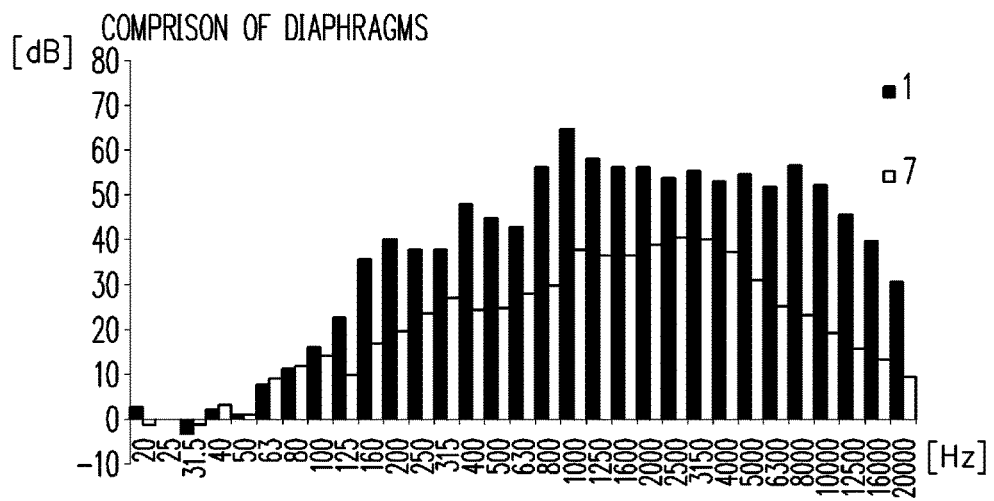
FIG. 19 is a comparative diagram in which the noises of a conventional article and the breast pump according to the first embodiment were subjected to a one-third octave analysis.
Figure 20:
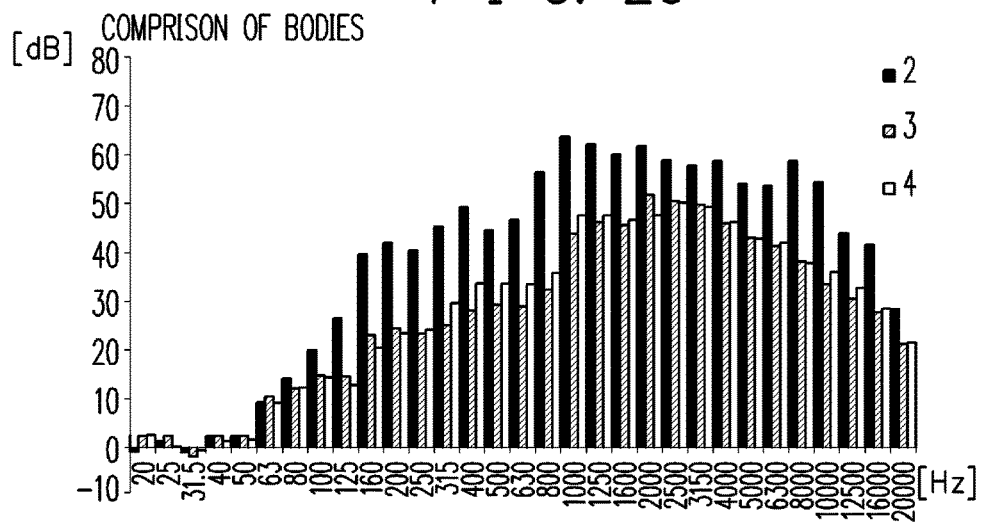
FIG. 20 is a comparative diagram in which the noises of a conventional article and the breast pumps according to the second and third embodiments were subjected to a one-third octave analysis.
Figure 21:
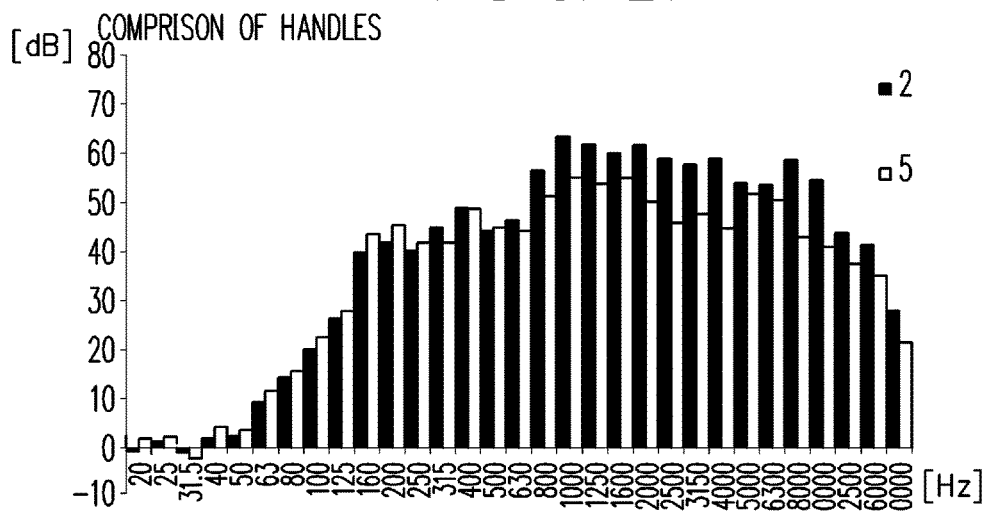
FIG. 21 is a comparative diagram in which the noises of the conventional article and the breast pump according to the fourth embodiment were subjected to a one-third octave analysis.

FIG. 18 shows experimental results obtained when experiments were conducted using the respective breast pumps in FIG. 17 and is a comparative diagram in which noise levels free from background noises are compared with each other. Further, FIG. 19 is a comparative diagram in which the noises of the conventional article and the breast pump according to the first embodiment were subjected to a one-third octave analysis. FIG. 20 is a comparative diagram in which the noises of the conventional article and the breast pumps according to the second and third embodiments were subjected to a one-third octave analysis. FIG. 21 is a comparative diagram in which the noises of the conventional article and the breast pump according to the fourth embodiment were subjected to a one-third octave analysis. Note that the numbers shown in FIGS. 18 to 21 correspond to the breast pumps of the first to seventh types in FIG. 17.

As shown in FIG. 18, the experimental results show that the noise levels of the breast pumps (the sixth and seventh types in FIG. 18) of the first embodiment were about 23 dB and reduced by about 50% compared with noise levels about 44 dB of the conventional breast pumps. It was found from the above results that the colliding part (the colliding part protruding from the diaphragm) used in the first embodiment produced the highest effect.

In addition, as shown in FIG. 19, the colliding part (the colliding part protruding from the diaphragm) used in the first embodiment produced the highest effect also for a high-frequency sound harsh to a user.

As shown in FIG. 18, the breast pumps (the third and fourth types in FIG. 18) of the second and third embodiments produced the second-highest effect and reduced its noise by about 23% compared with the conventional breast pumps.

In this regard, the colliding part 82 of the third embodiment has the "damper structure" in addition to the "cover structure" of the colliding part 80 of the second embodiment as shown in FIG. 13, but its noise level was 31.8 dB lower by only 0.1 dB than the noise level of the second embodiment 31.9 dB.

In addition, as shown in FIG. 20, there is little difference between the second embodiment and the third embodiment about a high-frequency sound harsh to a user. Rather, it was found that the breast pump 110 (see FIG. 11) of the second embodiment in which the colliding part has only "the cover structure (the configuration in which the colliding part is arranged inside the cavity part of the handle during a collision without having the through-hole as shown in FIG. 13)" has a band in which a high-frequency sound is reduced. Probably, this is because the colliding part 82 of the third embodiment shown in FIG. 13 has the thin portion 83 so as to be deformable and thus a high sound is easily generated correspondingly.

As shown in FIG. 18, the breast pump (the fifth type in FIG. 18) of the fourth embodiment produced the third-highest effect. Thus, it was found that the spring-shaped colliding part provided on the surface of the handle that is exposed to the outside had a certain influence on quietness. In addition, as shown in FIG. 21, it was found that the fourth embodiment had a certain influence on a high-frequency sound harsh to a user.

The present invention is not limited to the above respective embodiments.

For example, in the breast pump 20 of the first embodiment, the colliding part 40 that protrudes from the connecting region 37 of the diaphragm 30 collides against the end surface 67 of the handle 61 as shown in FIG. 5. However, the present invention is not limited to this, and the handle 61 and/or the colliding part 40 may have a different shape so that the colliding part 40 collides against the inside surface (the surface inside the cavity part S7) of the handle 61. Thus, since a noise reduction effect due to the covering effect is also produced in addition to the damper structure of the first embodiment, the breast pump having higher quietness can be provided. On this occasion, as shown in FIG. 2, a rib 93 (shown by imaginary lines) that protrudes toward the colliding part 40 during a collision is preferably formed (the whole rib 93 is preferably arranged inside the cavity S7) on the inside surface 61c of the handle 61 to allow the end surface of the rib 93 and the end surface of the colliding part 40 to collide against each other (in other words, when the deformation easiness of the diaphragm 30 is used as the damper structure, the colliding parts may protrude from both the diaphragm 30 and the handle 61). Thus, in FIG. 2, the likelihood of an adverse effect on the original function of the diaphragm 30 as the negative-pressure generating means can be further prevented with a reduction in the protruding width of the colliding part 40.

In addition, when the damper structure using the diaphragm 30 is provided, at least a part of the collided part serves as the connecting region 37 of the diaphragm 30 in FIG. 10. However, the present invention is not limited to this, and the whole collided part may be the portion of the diaphragm 30 other than the connecting region 37. For example, the thickness of the first wall part 31 may be greater than a conventional thickness. Thus, even if the colliding part 90 collides against only the first wall part 31 of the diaphragm 30, a quietness function can be effectively exhibited, while an adverse effect on the negative-pressure generating function of the diaphragm 30 is suppressed.

REFERENCE SIGNS LIST

11 Bottle
16 Hood
20, 100, 110, 120, 130, 140 Breast pump
21 Body
30 Diaphragm
37 Connecting region
40, 50, 80, 82, 84, 90 Colliding part
41 Base part
49 Support shaft part
61 Handle
79, 86 Through-hole
S4 Communicating part
S7 Cavity part

The invention claimed is:
1. A manual breast pump comprising:
a body having a communicating part configured to communicate with space surrounded by a hood placed on a breast;
a diaphragm configured to deform to generate a negative pressure in the communicating part;
a handle for operation configured to approach and separate from the body to deform the diaphragm, the handle having a lift part that is arranged above the diaphragm to lift and thereby deform the diaphragm and further having a lever part that turns from the lift part and extends adjacent a side surface of the body, the lever part approaching the body when the lift part lifts and thereby deforms the diaphragm in order to generate the negative pressure; and
an arm that extends from the body, having a support shaft part that is in a shaft shape; wherein
the handle has a fulcrum portion at which the handle is rotatably attached to the support shaft part,
the fulcrum portion of the handle is positioned between the lift part and the lever part such that the fulcrum portion of the handle is a fulcrum around which the handle is configured to pivot,
a colliding part, against which a region of the handle is configured to collide before the lever part of the handle and the body directly contact each other when the lever part approaches the body, is provided in at least a region of either the body or the diaphragm wherein the region of the handle that is configured to collide with the colliding part is defined as a collided region,
the colliding part is integrally made of a same material as a material of at least the region of either the body or the diaphragm that the colliding part is provided in, and
the colliding part has a damper structure configured to absorb an impulsive force generated when making a collision against the collided region or to reduce propagation of the impulsive force.
2. The manual breast pump according to claim 1, wherein the lever part of the handle has an elastic force in a direction in which the handle approaches the body, and exhibits the elastic force to be capable of contacting the body after the colliding part collides against the collided region.
3. The manual breast pump according to claim 1, wherein the colliding part has a through-hole, and a colliding side relative to the through-hole is deformable toward a side of the through-hole during the collision against the collided region.
4. The manual breast pump according to claim 1, wherein the colliding part is provided only in the region of the diaphragm, and the region of the diaphragm is located at a side close to the lever part of the handle.
5. The manual breast pump according to claim 1, wherein the lift part directly connects to the diaphragm, and the lever part has a designed shape to fit user's fingers.
6. The manual breast pump according to claim 1, wherein the colliding part is structured to be covered via a gap so as to be spaced from an outside via the gap when the handle collides against the colliding part.
7. The manual breast pump according to claim 6, wherein the handle has a cavity part opened toward a side of the body, and the colliding part is arranged inside the cavity part at least during the collision against the collided region.
8. The manual breast pump according to claim 7, wherein the handle is rotatable about a support shaft part of the body, and the colliding part is provided around the support shaft part of the body.
9. The manual breast pump according to claim 1, wherein the body has a base part that has higher rigidity than the diaphragm and serves as a base to which the diaphragm is connected, the colliding part is provided in the diaphragm, and the impulsive force generated when the colliding part makes the collision against the collided region is configured to act on a connecting region of the diaphragm that is connected to the base part.

10. The manual breast pump according to claim 9, wherein
the colliding part has a protrusion that protrudes from a circumference of the connecting region surrounding the base part.

11. The manual breast pump according to claim 9, wherein
the colliding part has a protrusion that protrudes from the connecting region so as to be capable of colliding against the handle.

12. The manual breast pump according to claim 11, wherein
the colliding part has a notched part or a concave part at a root or a halfway point thereof in a direction in which the protrusion extends.

13. A manual breast pump comprising:
a body having a communicating part configured to communicate with space surrounded by a hood placed on a breast;
a diaphragm configured to deform to generate a negative pressure in the communicating part;
a handle for operation configured to approach and separate from the body to deform the diaphragm, the handle having a lift part that is arranged above the diaphragm to lift and thereby deform the diaphragm and further having a lever part that turns from the lift part and extends adjacent a side surface of the body, the lever part approaching the body when the lift part lifts and thereby deforms the diaphragm in order to generate the negative pressure; and
an arm that extends from the body, having a support shaft part that is in a shaft shape; wherein
the handle has a fulcrum portion at which the handle is rotatably attached to the support shaft part,
the fulcrum portion of the handle is positioned between the lift part and the lever part such that the fulcrum portion of the handle is a fulcrum around which handle is configured to pivot,
a colliding part, against which the handle is configured to collide before the lever part of the handle and the body directly contact each other when the lever part approaches the body, is provided in at least a region of the handle,
the colliding part is integrally made of a same material as a material of at least the region of the handle, and
the colliding part has a damper structure configured to absorb an impulsive force generated when making a collision or to reduce propagation of the impulsive force.

14. The manual breast pump according to claim 13, wherein
the colliding part is a protruding part that protrudes from the handle,
at least a part of the collided region is a connecting region of the diaphragm, and
the colliding part is configured to collide against a surface in a thickness direction of a collided region.

15. The manual breast pump according to claim 13, wherein
the colliding part is structured to be covered via a gap so as to be spaced from an outside via the gap when the handle collides against the colliding part.

16. The manual breast pump according to claim 13, wherein
the handle has a cavity part opened toward a side of the body, and
the colliding part is arranged inside the cavity part at least during the collision.

17. The manual breast pump according to claim 13, wherein
the colliding part has a through-hole, and a colliding side relative to the through-hole is deformable toward a side of the through-hole during the collision.

18. The manual breast pump according to claim 13, wherein
the lift part directly connects to the diaphragm, and
the lever part has a designed shape to fit user's fingers.

* * * * *